(12) United States Patent
Neumann

(10) Patent No.: US 12,176,092 B2
(45) Date of Patent: Dec. 24, 2024

(54) SYSTEMS AND METHODS FOR GENERATING A HEMATOLOGICAL PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

( * ) Notice: Subject to any disclaimer, the term of this patent is extended or adjusted under 35 U.S.C. 154(b) by 519 days.

(21) Appl. No.: 17/164,511

(22) Filed: Feb. 1, 2021

(65) Prior Publication Data
US 2022/0246274 A1 Aug. 4, 2022

(51) Int. Cl.
| G06Q 10/00 | (2023.01) |
| A61B 5/00 | (2006.01) |
| G16H 10/60 | (2018.01) |
| G16H 20/60 | (2018.01) |
| G16H 50/20 | (2018.01) |
| G16H 50/70 | (2018.01) |

(52) U.S. Cl.
CPC ........... *G16H 20/60* (2018.01); *A61B 5/4866* (2013.01); *A61B 5/7267* (2013.01); *G16H 10/60* (2018.01); *G16H 50/20* (2018.01); *G16H 50/70* (2018.01)

(58) Field of Classification Search
CPC ........ G16H 10/60; G16H 50/70; G16H 50/20; G16H 20/60; G26H 20/60
See application file for complete search history.

(56) References Cited

U.S. PATENT DOCUMENTS

| 8,000,982 B2 | 8/2011 | Kane |
| 8,589,082 B2 | 11/2013 | Chakrabarty |
| 8,762,167 B2 | 6/2014 | Blander |
| 2012/0054642 A1* | 3/2012 | Balsiger ................ G06Q 10/10 715/752 |

(Continued)

FOREIGN PATENT DOCUMENTS

WO 2018204763 11/2018

OTHER PUBLICATIONS

By: Kenneth Westerman, Longitudinal analysis of biomarker data from a personalized nutrition platform in healthy subjects. Sci Rep 8, 14685 (2018). https://doi.org/10.1038/s41598-018-33008-7https://www.nature.com/articles/s41598-018-33008-7.

*Primary Examiner* — Rajesh Khattar
(74) *Attorney, Agent, or Firm* — Caldwell Intellectual Property Law

(57) ABSTRACT

A system for generating a program includes a computing device configured to acquire at least a hematological datum, retrieve a hematological profile as a function of the at least a hematological datum, classify the hematological profile to a hematological disorder bundle, determine, using the hematological disorder bundle and the hematological profile, at least a nutritional level, wherein determining includes identifying a hematological relationship relating an effect of a plurality of nutritional levels on the hematological disorder bundle and determining the at least a nutritional level as a function of the hematological relationship and the hematological profile, identify, using the at least a nutritional level, at least a nutrition element, and generate a consumption program as a function of the at least a nutrition element.

20 Claims, 8 Drawing Sheets

(56) References Cited

U.S. PATENT DOCUMENTS

| | | | |
|---|---|---|---|
| 2013/0018651 A1* | 1/2013 | Djordjevic | G06Q 10/00 |
| | | | 704/9 |
| 2017/0147941 A1* | 5/2017 | Bauer | G06N 20/10 |
| 2018/0233223 A1 | 8/2018 | Solari | |
| 2018/0240542 A1* | 8/2018 | Grimmer | A61P 25/00 |
| 2020/0043593 A1 | 2/2020 | Alptekin | |
| 2020/0066181 A1 | 2/2020 | Hadjigeorgiou | |
| 2020/0168314 A1 | 5/2020 | Rezzi | |
| 2020/0356864 A1 | 11/2020 | Neumann | |
| 2021/0050086 A1* | 2/2021 | Rose | G16H 20/30 |
| 2022/0344049 A1* | 10/2022 | Hall | G06N 3/0464 |

* cited by examiner

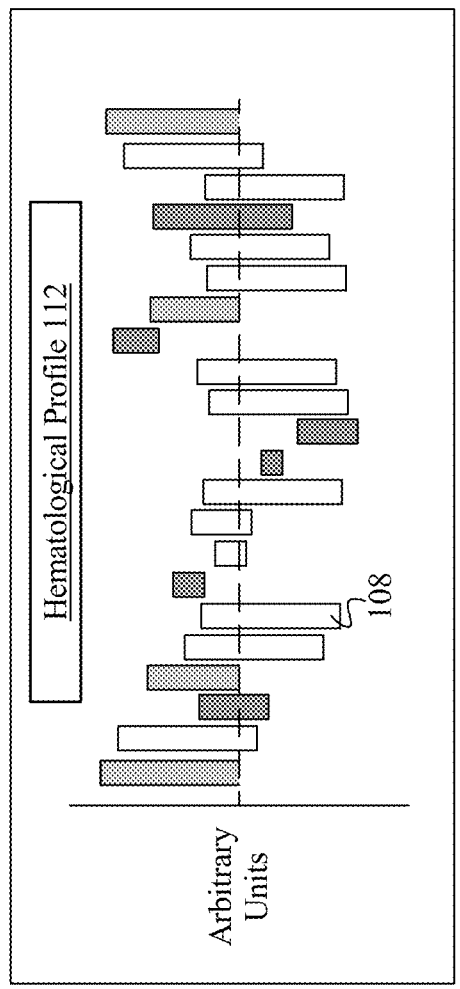 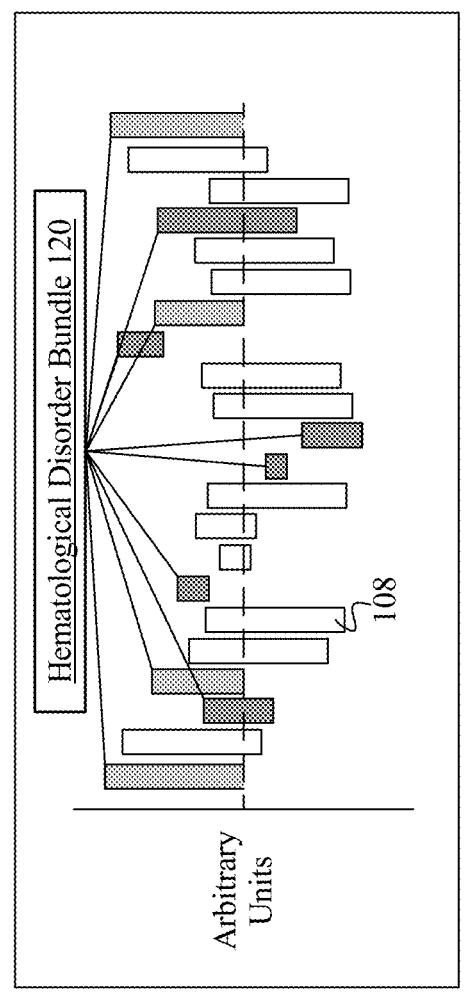

SYSTEMS AND METHODS FOR GENERATING A HEMATOLOGICAL PROGRAM

FIELD OF THE INVENTION

The present invention generally relates to the field of nutrition programming for addressing hematological disorders. In particular, the present invention is directed to systems and methods for generating a hematological program.

BACKGROUND

Efficient systems for tracking age-related biological degradations suffer from difficulties in adequately sampling the breadth of physiological parameters that relate to degradation over the lifetime of the subject. Furthermore, systems have difficulty in efficiently and properly identifying the ways in which degradations occur, capturing the amounts of degradation and rates of degradation, and predicting degradation trajectories from these confounding variables.

SUMMARY OF THE DISCLOSURE

In an aspect, a system for generating a program for addressing hematological disorders using machine-learning including a computing device configured to acquire at least a hematological datum relating to a subject, retrieve a hematological profile related to the subject as a function of the at least a hematological datum, classify the hematological profile to a hematological disorder bundle, determine, using the hematological disorder bundle and the hematological profile, at least a nutritional level, wherein determining the at least a nutritional level includes identifying a hematological relationship, wherein the hematological relationship relates an effect of a plurality of nutritional levels on the hematological disorder bundle, and determining the at least a nutritional level as a function of the hematological relationship and the hematological profile, identify, using the at least a nutritional level, at least a nutrition element, and generate a consumption program as a function of the at least a nutrition element.

In another aspect, a method for generating a program for addressing hematological disorders using machine-learning including acquiring, by a computing device, at least a hematological datum relating to a subject, retrieving, by the computing device, a hematological profile related to the subject as a function of the at least a hematological datum, classifying, by the computing device, the hematological profile to a hematological disorder bundle, determining, by the computing device, using the hematological disorder bundle and the hematological profile, at least a nutritional level, wherein determining the at least a nutritional level includes identifying a hematological relationship, wherein the hematological relationship relates an effect of a plurality of nutritional levels on the hematological disorder bundle, and determining the at least a nutritional level as a function of the hematological relationship and the hematological profile, identifying, by the computing device, using the at least a nutritional level, at least a nutrition element, and generating, by the computing device, a consumption program as a function of the at least a nutrition element.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 4A-B are a diagrammatic representations of exemplary embodiments of a hematological profile;

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a hematological program for addressing hematological disorders using machine-learning. In an embodiment, system includes a computing device configured to receive hematological indicators of a subject. Hematological indicators may include experimental testing results, genotypic and phenotypic analysis, and the like. Computing device is configured to retrieve a hematological profile corresponding to the subject. Computing device may generate the hematological profile by using a machine-learning algorithm indicating possible mathematical relationships linking values to model hematological indicators to hematological parameters, where hematological parameters may be compared to threshold values indicating normal ranges. Computing device may assign the hematological profile to a hematological disorder grouping, for instance using a machine-learning classifier according to subsets of a plurality of subjects. Computing device is configured to determine at least a nutritional level by identifying a hematological relationships. Hematological relationships may be identified by generating a hematologic model to correlate the magnitude of effect of nutrients to data in the hematological profile. Computing device may determine at least a nutrition element as a function of the nutritional level. Computing device may generate a hematological program using a linear programming function to generate an ordering of nutrition elements as a function of a consumption program. In an embodiment, computing device may provide nutrition elements to a subject device via a graphical user interface and provide a hematological metric that relate the hematological state of the subject according to nutrition.

Figure 1:
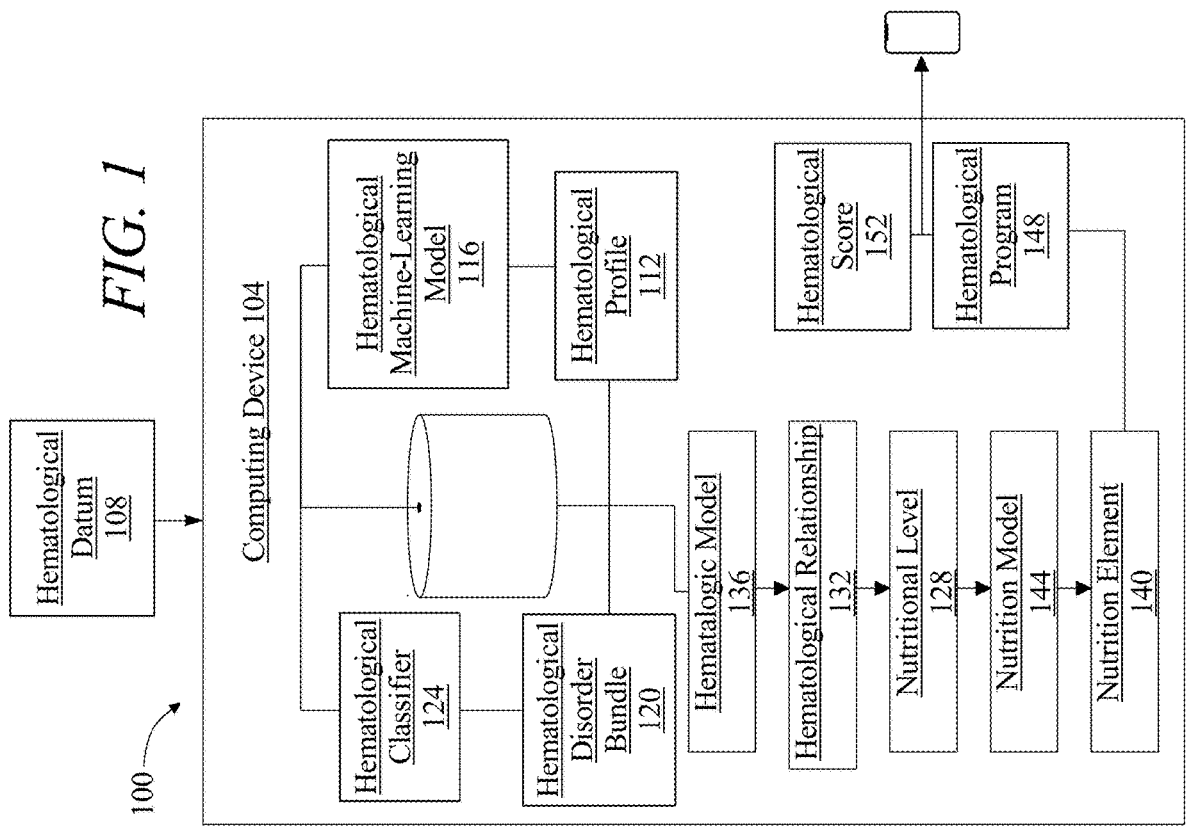
FIG. 1 is a block diagram illustrating a system for generating a hematological program.

Referring now to FIG. 1, an exemplary embodiment of a system 100 for generating a hematological program for addressing hematological disorders using machine-learning is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software, and the like) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device is configured to receive at least a hematological datum from a subject. A "hematological datum," as used in this disclosure, is a biological and/or chemical substance or process that is indicative of presence of hematological function in the body, and/or one or more aspects thereof. Hematological datum 108 may include biological molecules and/or biomarkers existing within a normal cell, a stressed cell, disease state cell, and/or a specific response of the body indicative of deterioration and/or aging. Receiving the at least a hematological datum 108 may include receiving a result of one or more tests relating to the subject, such as a blood panel, blood glucose test, lipid panel, and the like. Tests may include serological tests, measurements of blood oxygen levels, stress tests, symptoms, activities, or recent travel, tests for blood-borne pathogens, tests for bone-marrow or blood-related disorders or cancers, or the like Hematological datum 108 may include test results of screening and/or early detection of hematological disease, diagnostic procedures, prognostic indicators from other diagnoses, such as Sickle cell anemia, from predictors identified in a medical history, and physiological data and data relating to biomolecules associated with and/or found within the blood of a subject such as physiological parameters including systolic and diastolic blood pressure; blood metabolites such as homocysteine, creatinine, low-density lipoprotein (LDL), very low density lipoprotein (VLDL), high-density lipoprotein (HDL), triglycerides, fasting glucose, glycosylated hemoglobin (HbA1c); blood hormonal profile including leptin, adiponectin, testosterone, cortisol; immunological and disease state indicators in the blood such as c-reactive protein, IL-6, fibrinogen, albumin, TNF-α, serum amyloid A, T cell concentration/ratio, Amyloid B42, DHEA-S, IGF-1; indicators of oxidative stress such as reactive oxygen species, superoxide dismutase, and the like. Hematological datum 108 may include, without limitation, biomarkers such as VEGF, CRP, IL-10, IL-1B, sROBO-4, VTE, Prothrombin, F1, F2, Factor V Leiden, protein C, protein S, APLA, APCR, FMD, TGF-B, transferrin, ferritin, TNF-alpha, serum osteocalcin, bone-specific alkaline phosphatase, type I procollagen carboxy-terminal pro-peptide, urine-free deoxypyridoline, N-telopeptide, C-telopeptide. A person skilled in the art, having the benefit of the entirety of this disclosure, will be aware of various additional tests and/or data that may be used and or received as hematological datum 108.

Continuing in reference to FIG. 1, hematological datum 108 may include results and or analysis enumerating the identification of nucleic acids in the blood. Hematological datum 108 may include the presentation of single nucleotide polymorphisms (SNPs), mutations, chromosomal deletions, inversions, translocation events, and the like, in genetic sequences isolated from the blood that may be indicative of hematological disorders. Hematological datum 108 may include epigenetic factors such as patterns of microRNAs (miRNAs). Hematological datum 108 may include hematological analysis including results from T-cell activation assays, abnormal nucleation of white blood cells, white blood cell counts, concentrations, recruitment and localization, and the like. Hematological datum 108 may be received as a function of a subject indicating a prior diagnosis, treatment received, among other data indicated in a medical history, physician's assessment, and the like. Hematological datum 108 may include any symptoms, side effects, and co-morbidities associated with and relating to treatment regimens, recovery from injury and/or illness, edema formation, and the like. Hematological datum 108 may be received and/or identified from a biological extraction of a subject, which may include analysis of a physical sample of a subject such as blood, DNA, and the like, without limitation and as described in U.S. Nonprovisional application Ser. No. 16/886,647, filed May 28, 2020, and entitled, "METHODS AND SYSTEMS FOR DETERMINING A PLURALITY OF BIOLOGICAL OUTCOMES USING A PLURALITY OF DIMENSIONS OF BIOLOGICAL EXTRACTION SUBJECT DATA AND ARTIFICIAL INTELLIGENCE," the entirety of which is incorporated herein by reference.

Continuing in reference to FIG. 1, hematological datum 108 may be organized into training data sets. "Training data," as used herein, is data containing correlations that a machine learning process, algorithm, and/or method may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below.

Continuing in reference to FIG. 1, hematological datum 108 may be used to generate training data for a machine-learning process. A "machine learning process," as used in this disclosure, is a process that automatedly uses a body of data known as "training data" and/or a "training set" to generate an algorithm (such as a collection of one or more functions, equations, and the like) that will be performed by a machine-learning module to produce outputs given data provided as inputs; this is in contrast to a non-machine learning software programing where the commands to be executed are determined in advance by a subject and written in a programming language, as described in further detail below.

Continuing in reference to FIG. 1, hematological datum 108 may be organized into training data sets and stored and/or retrieved by computing device 104, without limitation, as a relational database, a key-value retrieval database such as a NOSQL database, or any other format or structure for use as a database that a person skilled in the art would recognize as suitable upon review of the entirety of this disclosure. Hematological datum 108 training data may alternatively or additionally be implemented using a distributed data storage protocol and/or data structure, such as a distributed hash table and the like. Hematological datum 108 training data may include a plurality of data entries and/or records, as described above. Data entries may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries of hematological data may be stored, retrieved, organized, and/or reflect data and/or records as used herein, as well as categories and/or populations of data consistent with this disclosure.

Continuing in reference to FIG. 1, computing device is configured to retrieve a hematological profile related to the subject as a function of at least a hematological datum. A "hematological profile," as used in this disclosure, is a profile that enumerates hematological data in the subject; hematological profile may include one or more quantities, aggregations, or other quantitative representations of one or more elements and/or types of hematological data, and may be retrieved, without limitation, from records in a database, which may be implemented in any manner suitable for implementation of a database as described in this disclosure, via reception from a remote device, or the like. At least a hematological datum may be used, without limitation, as a query for retrieval of hematological profile 112. Hematological profile 112 may include at least a degradation rate which may be an instantaneous rate or a rate that is over a variable range of time. Hematological profile 112 may include thresholds, ranges of numerical values, binary determinations, and the like, which summarize the current hematological profile of the subject.

Continuing in reference to FIG. 1, hematological profile 112 may include any number of hematological parameters. A "hematological parameter," as used in this disclosure, is a metric that describes the presence of at least a hematological datum 112. For instance and without limitation, a hematological parameter may enumerate concentrations of blood metabolites relative to a threshold value in a cohort of healthy adults. In such an instance, the hematological parameter may be a small positive numerical value for biomarkers within the "healthy" or "normal" range, large positive numerical value for concentration indicating exceptional health, and negative values indicating a deficiency or alarming increase relating to the normal threshold range or value. Hematological parameter may be biomarker-specific, for instance and without limitation, a numerical value for each of 100+ types of biomarker categories, where each numerical value communicates a likelihood that a hematological datum 108 relates to a normal/healthy state, an abnormal state, a particular disorder, among other categorizations. Hematological profile 112 may include any medical, physiological, biological, chemical, and/or physical determination about the current state of a subject's propensity for hematological disease, including projected, future likelihood for disease. Hematological profile 112 may include qualitative and/or quantitative metrics of the presence of symptomology, development of disease, biomarkers indicative of disease, biomarkers classified to subcategories, and the like. Hematological profile 112 may include qualitative determinations, such as binary "yes"/"no" determinations for particular types, "normal"/"abnormal" determinations about the presence of and/or concentration of hematological data 108, for instance as compared to a normalized threshold value of a biomarker among healthy adults. Hematological profile 112 may include a plurality of hematological parameters, wherein hematological parameters are quantitative determinations such as a "hematological scoring", which may include any metric, parameter, or numerical value that communicates a value relating to a biomarker. Hematological profile 112 may include hematological parameters that are mathematical expressions relating the current degradation state. Hematological profile 112 may include mathematical expression interrelating combinations of biomarkers as they may relate to clinical significance. Computing device 104 may retrieve hematological profile 112 from a database, as described in further detail below.

Continuing in reference to FIG. 1, retrieving hematological profile 112 may include a process of searching for, locating, and returning hematological profile 112 data. For example, hematological profile 112 may be retrieved as documentation on a computer to be viewed or modified such as files in a directory, database, and the like. In non-limiting illustrative embodiments, computing device 104 may locate and download hematological profile 112 via a web browser and the Internet, receive as input via a software application and a subject device, via a telemedicine platform from a physician, lab technician, shared data storage point, and the like.

Continuing in reference to FIG. 1, retrieving hematological profile 112 may include receiving data via a graphical user interface. A "graphical user interface," as used in this disclosure, is any form of a subject interface that allows a subject to interface with an electronic device through graphical icons, audio indicators, text-based interface, typed command labels, text navigation, and the like, wherein the interface is configured to provide information to the subject and accept input from the subject. Graphical user interface may accept input, wherein input may include an interaction with a subject device. A subject device, as described in further detail below, may include computing device 104, a "smartphone," cellular mobile phone, desktop computer, laptop, terminal, tablet computer, internet-of-things (IOT) device, wearable device, among other devices. Subject device may include any device that is capable for communicating with computing device 104, database, or able to receive data, retrieve data, store data, and/or transmit data, for instance via a data network technology such as 3G, 4G/LTE, 5G, Wi-Fi (IEEE 802.11 family standards), and the like. Subject device may include devices that communicate using other mobile communication technologies, or any combination thereof, for short-range wireless communication (for instance, using Bluetooth and/or Bluetooth LE standards, AirDrop, Wi-Fi, NFC, and the like), and the like.

Still referring to FIG. 1, retrieving the hematological profile 112 related to the subject may include training a hematological machine-learning model with the training data that includes a plurality of data entries wherein each entry correlates hematological data to a plurality of hematological parameters. Computing device 104 may generate the hematological profile 112 as a function of the hematological machine-learning model and at least a hematological datum 108. Hematological machine-learning model 116 may include any machine-learning process, algorithm, and/or model as performed by machine-learning module, described in further detail below. Relationships observed in training data to enumerate hematological parameters for hematological profile 112 may be used to statistically relate hematological determinations for which no directly observable data exists. For instance and without limitation, a combination of biomarkers relating to interleukins, prostaglandins, cytokines, complement pathway molecules such as C-reactive proteins, tumor necrosis factor, cellular stress markers, among other biomarkers, may indicate the presence of blood-borne parasites such as malaria, blood-borne viruses (BBVs) such as hepatitis V, hepatitis C, and HIV, of which there is no direct biochemical observation of.

Continuing in reference to FIG. 1, training data for hematological machine-learning model 116 may include hematological data 112 organized into training data sets, as described above, including results from biological extraction samples, health state questionnaires regarding symptomology, medical histories, physician assessments, lab work, and the like. Training data may be retrieved from a database, as described in further detail below. Hematological profile 112 training data may originate from the subject, for instance via a questionnaire and a subject interface with computing device 104, for subject to provide medical history data and/or symptoms. Receiving hematological profile training data may include receiving whole genome sequencing, gene expression patterns, and the like, for instance as provided by a genomic sequencing entity, hospital, database, the Internet, and the like. Hematological profile 112 training data may include raw data values recorded and transmitted to computing device 104 via a wearable device such as a bioimpedance device, ECG/EKG/EEG monitor, physiological sensors, blood pressure monitor, blood sugar and volatile organic compound (VOC) monitor, and the like. Hematological profile 112 training data may include inputs directly into system 100 that originate from an individual other than subject, including for instance a physician, lab technician, nurse, dietician, strength coach, psychologist, and the like. Hematological profile 112 may be input directly into system 100 by these personnel. Alternatively or additionally, training data for generating hematological profile 112, such as raw data values, may be input into system 100 by such personnel. It is important to note that training data for machine-learning processes, algorithms, and/or models used within system 100 herein may likewise originate from any source described for hematological profile 112 training data.

Continuing in reference to FIG. 1, hematological profile machine-learning model 116 may include any machine-learning algorithm such as K-nearest neighbors algorithm, a lazy naïve Bayes algorithm, among other algorithms, machine-learning process such as supervised machine-learning, unsupervised machine-learning, or method such as neural nets, deep learning, and the like. Hematological profile machine-learning model 116 may be trained to derive an equation, function, series of equations, or any mathematical operation, relationship, or heuristic, that can automatedly accept an input, such as hematological datum(s) 108, and correlate, classify, or otherwise calculate an output, such as hematological parameter(s). Hematological profile machine-learning model 116 may include individual functions, derived for unique relationships observed from the training data for each hematological datum 108. In non-limiting illustrative examples, the parameters involved in a variety of physiological tests, as identified above, may be retrieved from a database, such as a repository of peer-reviewed research (e.g. National Center for Biotechnology Information as part of the United States National Library of Medicine), and the hematological profile machine-learning model 116 may derive an algorithm which determines an average and statistical evaluation (mean±S.D.) calculated from the data, across which the subject's parameters may be compared. In such an example, hematological profile machine-learning model 116 may derive an algorithm according to the data used to derive the average and statistical evaluation changes as a function of the subset of data to which the subject is to be compared, for instance and without limitation, based on age, fitness level, nutrition deficiency, symptomology, past diagnoses, and the like.

Continuing in reference to FIG. 1, computing device 104 is configured to classify the hematological profile 112 to a hematological disorder bundle. A "hematological disorder bundle," as used in this disclosure, is a determination about a current hematological state of the subject. Hematological disorder bundle 120 may include any diagnosis (current disorder), prognosis (predicted future diagnoses, outcomes, and the like), current risk, and/or future risks. Hematological disorder bundle 120 may include pathological, histological, and/or clinical classification identifiers such as "abnormal white blood cell count (WBC)", "low red blood cell count (RBC)", "prothrombin time (PT) of 13 seconds", and the like. Hematological disorder bundle 120 may include classification to category of disorders such as β-thalassemia, α-thalassemia, Sickle cell anemia, G6PD, ITP, hemophilia A/B, aplastic anemia, AIA, FA, "other HA", AFI, thrombasthenia, spherocytosis, vonWillibrand disease, Gaucher, marble bone disease, pure red cell aplasia, among others. Hematological disorder bundle 120 may include identifiers associated with disorders, conditions, symptoms, and the like, which may correspond with categorization. Hematological disorder bundle 120 may include a predictive classification, where a subject such as a healthy young adult, does not harbor hematological datum(s) 108 indicative of obvious current hematological disorder but may include data that indicates a hematological disorder bundle 120 with which they may be most closely categorized to, and/or an imminent categorization. Hematological profile 112 may have associated with it an identifier, such as a diagnostic label, that corresponds to a hematological disorder bundle 120. Hematological disorder bundle 120 may be stored and/or retrieved from a database.

Continuing in reference to FIG. 1, classifying the hematological profile 112 to a hematological disorder bundle 120 may include training a hematological classifier using training data which includes a plurality of data entries of hematological profile data from a subset of categorized subjects. A "hematological classifier," as used in this disclosure, is a machine-learning classifier that sorts hematological profile 112 to hematological disorder bundle 120. A classifier may include a machine-learning model, such as a mathematical model, neural net, or program generated by a machine learning algorithm known as a "classification algorithm," as described in further detail below. Hematological classifier 124 may be generated by a hematological classification machine-learning process, which may include any machine-learning algorithm, process, and/or model described herein performed by a machine-learning module, as described in further detail below. Hematological classification machine-learning process may generate hematological classifier 124 using training data. Training data may include identification of particular biomarkers, threshold values associated with each, and/or hematological parameters that would classify a subject in a particular disorder category. Training data may include a plurality of data values relating biomarkers to disorders, where each biomarker is assigned a variable, and the variables may be used in an empirical formula for determining the presence of a disorder or applying a particular diagnosis. Hematological classifier 124 may sort inputs, such as hematological profile 112, into categories or bins of data, such as classifying the data into hematological disorder bundle 120, outputting the bins of data and/or labels associated therewith.

Continuing in reference to FIG. 1, training data for hematological classifier 124 may include a set of hematological data 108 as it relates to classes of disorder types, disease types, and the like. For instance and without limitation, training data may include ranges of hematological data 108 as they correlate to various degrees of anemia, wound healing, immunological function, and the like. Such training data may include hematological data 108 as it relates to hematological disorder bundle 120 for subsets of a plurality of subjects, segmented according to subject characteristics such as smoking, exercise, diet, age, sex, alcohol consumption, ethnicity, nutritional deficiency, co-morbidities, and the like. Training data may be used by classification machine-learning process to train a classifier to derive relationships present in the data that may result in a machine-learning model that automatedly classifies a subject to a hematological disorder bundle 120 as a function of the data present in their hematological profile 112. Training data may originate from any source described herein, for instance retrieved from a database, retrieved via a web browser and the Internet, peer-reviewed research repository, clinical data, subject input data, wearable device, physiological sensor, medical history data, and the like.

Continuing in reference to FIG. 1, hematological classifier 124 may be configured to output at least a datum that labels or otherwise identifies a set of data that are clustered together, found to be close, relate to one another via a metric, scoring, probability, and the like, as described below. Machine-learning module, as described in further detail below, may generate a classifier using a classification algorithm, defined as a process whereby computing device and/or any module and/or component operating thereon derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, a hematological profile 112 training data classifier may classify elements of training data to elements that characterizes a sub-population, including subset of hematological datum 108 such as gene expression patterns and epigenetic markers as it relates to a variety of disorder types and/or other analyzed items and/or phenomena for which a subset of training data may be selected.

Continuing in reference to FIG. 1, classifying hematological profile 112 to hematological disorder bundle 120 may include generating a threshold value of a hematological datum 108, wherein the threshold value indicates a value for comparing the hematological datum 108 for determining the presence of a hematological disorder. Computing device 104 may search, identify, and retrieve a threshold value, for instance via a web browser and the Internet. Threshold value may indicate a numerical value, or range of numerical values, such as 11-12.5 seconds for prothrombin time (PT) and/or partial thromboplastin time (PTT) which indicates a normal amount of time for blood clotting. In such an example, deviations in clotting time may indicate increased risk of blood clot (quicker times) or increased risk of hemophilia or lack of blood clotting ability (longer times). Generating a threshold value may include calculating a threshold value. For instance, computing device 104 may retrieve PT and PTT data points for subsets of 18-25 year old men, exhibiting no nutritional deficiency, BMI between 15-20, who engage in regular physical activity to determine a threshold range of values for such biomarkers that may represent more accurate comparison for classification. In such an example, a time of 13.0 seconds may be "normal" among geriatrics, but instead relates to a time one standard deviation above average for a younger cohort, potentially indicating an issue. Computing device 104 may then classify subjects into cohorts of alike subsets according to comparison along the threshold. Classification in this manner may result in defining subsets of subjects for more accurately determining the presence of hematological disorder among the population, and more accurately identifying the presence of nutrition-related hematological functions.

Continuing in reference to FIG. 1, classifying hematological profile 112 to hematological disorder bundle 120 may include classifying the hematological profile 112 to the hematological disorder bundle 120 using the hematological classifier 124. Classification using hematological classifier 124 may include identifying which set of categories (hematological disorder bundle 120) an observation (hematological profile 112) belongs. Classification may include clustering based on pattern recognition, wherein the presence of hematological data 108, such as genetic indicators, symptoms, and the like, identified in hematological profile 112 relate to a particular hematological disorder bundle 120. Such classification methods may include binary classification, where the hematological profile 112 is simply matched to each existing hematological disorder bundle 120 and sorted into a category based on a "yes"/"no" match. Classification done in such a manner may include weighting, scoring, or otherwise assigning a numerical value to elements in hematological profile 112 as it relates to each disorder type and assign the subject to a hematological disorder bundle 120 that results in the 'highest' score, depending on the criteria for highest. Such a score may represent a likelihood, probability, or other statistical evaluation that relates to the classification into hematological disorder bundle 120.

Continuing in reference to FIG. 1, computing device 104 may assign the hematological disorder bundle 120 as a function of the classification. Classifying the hematological profile 112 (input) to a hematological disorder bundle 120 (output) may include classifying the hematological disorder bundle 120 as a function of the hematological classifier 124 generated by the hematological classification machine-learning process. Training data for hematological classifier 124 may include sets of hematological parameters and/or hematological data 108, as described above, correlated to hematological disorder bundle according to trends observed in the data for subsets of subjects. Such training data may be used to learn how to categorize a subject's hematological profile 112 to categories depending on trends in the data. In this way, hematological classifier 124 may also generate new degradation categories depending on how well a subject may "fit" within a particular classification.

Continuing in reference to FIG. 1, classifying may include classifying the hematological profile 112 to a nutrition-linked hematological disorder bundle. A "nutrition-linked hematological disorder bundle," as used in this disclosure, is a hematological disorder categorization that indicates a category which is sensitive to nutritional modification. Nutrition-linked hematological disorder bundle may include a category of current disorders that are not averse to nutritional modification, in that they may be address at least in part by varying nutrition levels in the subject. manipulation by varying nutritional consumption. A nutrition-linked hematological disorder bundle may include for instance and without limitation acute iron deficiencies, which may cause and/or exacerbate anemia, where iron supplementation may "cure" the deficiency where the disorder categorization may be changed with sufficient, sustained nutrient supplementation. Such classification may include identifying biomarkers or any hematological data 108 present in hematological profile 112 which are resistant to nutritional changes and identifying which can be addressed with nutritional modification, altering dietary habits, nutrient supplementation, and the like.

Continuing in reference to FIG. 1, classifying may include classifying the hematological profile 112 to a nutrition-linked disorder prevention bundle. A "nutrition-linked disorder prevention bundle," as used in this disclosure, is a hematological disorder categorization for which nutrients may act as a preventative measure. Nutrition-linked disorder prevention bundle may include a category which will occur, or is imminent, according to the hematological profile 112 of the subject which may be prevented or ameliorated from nutritional modification. A nutrition-linked disorder prevention bundle may include a risk for developing blood cancer in the future, where the risk of developing the blood cancer may be reduced from nutritional intervention. Classification to such a category may include identifying biomarkers, or any hematological datum 108, present in hematological profile 112 which may be modified, over time, with sustained, chronic nutrient manipulation.

Continuing in reference to FIG. 1, computing device 104 is configured to determine using the hematological disorder bundle 120 and the hematological profile 112, at least a nutritional level. A "nutrient," as used in this disclosure, is any biologically active compound whose consumption is intended for addressing hematological disorder. A "nutritional level," as used in this disclosure, is a range of nutrient amounts that are predicted to have an effect on a hematological datum 108 that results in a concomitant effect on hematological disorder bundle 120. Nutritional level 128 may include numerical values, ranges, functions, and/or any other mathematical arrangement describing nutrient amounts. Nutritional level 128 may relate to supplementary use of oral digestive enzymes. In such an instance, nutritional level 128 may relate to units of enzyme activity, specific activities, and the like. Nutritional level 128 may include probiotics which may also have merit as anti-hematological disorder measures. In such an instance, nutritional level 128 may include the identities of bacterial isolates, colony forming units (CFU/mL), and the like. Nutritional level 128 may include mass amounts of micronutrients such as vitamins, minerals, trace elements, electrolytes, such as selenium, folic acid, vitamin B-12, vitamin D, bicarbonate, calcium, and the like. Nutritional level 128 may include values relating to phytonutrients and plant-based biomolecules such as chlorophyll, antioxidants such as the carotenoids ($\alpha$-carotene, $\beta$-carotene, lycopene, lutein, cryptoxanthin), and the like. Nutritional level 128 may contain biologically active compounds that are not typically considered as part of recommended daily nutrients, nor are they intended to provide appreciable amounts of calories, such as phytonutrients, nutraceuticals, antioxidants, and the like; for instance and without limitation, *allium* and bioactive ingredients present in cruciferous vegetables such as broccoli sprouts, which are known sources of antioxidants such as sulforaphane, polyphenols present in fruits, vegetables, seeds, nuts, legumes, and the like.

Continuing in reference to FIG. 1, determining the at least a nutritional level 128 may include identifying a hematological relationship, wherein the hematological relationship relates an effect of a plurality of nutritional levels on the hematological profile and/or data in the hematological profile that relates to the hematological disorder bundle. A "hematological relationship," as used in this disclosure, is a correlation, or any mathematical relationship, which relates an effect of a plurality of nutritional levels on the data in the hematological profile that relates to the hematological disorder bundle. Hematological relationship 132 may be described by a vector, for instance with a direction and magnitude that describes if the disorder will improve or worsen, and by which amount according to the nutrient amount and the current nutritional level of the subject. Hematological relationships may include a function including a series of values that may be stored in a table in a database for all nutrient amounts to provide intended effect on a variety of hematological disorder bundles 120. In this way, for each subject classified to a hematological disorder bundle 120, a nutritional level 128 may be retrieved from the database. Hematological relationship 132 may include empirical formulas, for instance retrieved by computing device 104 using a web browser and the Internet, database, and the like, which inform correlations between nutrient consumption and hematological disorder.

Continuing in reference to FIG. 1, determining the hematological relationship 132 may include generating a hematologic model using training data, wherein training data includes a plurality of data entries correlating nutritional levels to effects on hematological data. Hematologic model may be generated using a hematologic model machine-learning process including any machine-learning algorithm, process, and/or model as performed by a machine-learning module, as described in further detail below. Hematologic model 136 may be trained using training data which originates from any source, as described herein, for instance and without limitation retrieved from a database, retrieved via a web browser and the Internet, peer-reviewed research repository, clinical data, subject input data, wearable device, physiological sensor, medical history data, and the like. Training data may include a plurality of data entries including ranges of values of nutrients, for a variety of nutrient types and classes such as water-soluble vitamins, fat-soluble vitamins, transition metal nutrients, trace metals, alkali earth metal nutrients, phytonutrients, essential amino acids, and the like, which are related to an effect on blood disorders such as chronic insulin resistance, anemia, and the like. Such training data may relate to the magnitude of effect of acute and chronic nutrient deficiencies over time. Training data may be segmented by cohort, where nutritional level 128 for large sets (>1,000+) of healthy subjects is compared to nutritional levels of cohorts of subjects classified by hematological disorder bundle 120 to calculate nutritional level 128 mismatch. Training data may be received as input from a user, physician, or the like, where nutritional level data inputs are gathered from a plurality of users. Training data may be stored and/or retrieved from a database, as described in further detail below. Training data may be received as wearable device data, physiological sensor data, retrieved via a web browser and the Internet, received as medical history data, and/or any other source described herein.

Continuing in reference to FIG. 1, computing device 104 is configured to the at least a nutritional level as a function of the hematological relationship 132 and the hematological profile 112. Hematologic model 136 may be trained to derive mathematical relationships observed in the training data to automatedly accept hematological profile 112 and/or hematological disorder bundle 120 inputs and calculate an output that is at least a nutritional level 128, of a plurality of nutritional levels 132. Nutritional level 128 outputs may include predicted effects on the hematological profile 112 and/or hematological disorder bundle 120. Hematologic model 132 may determine magnitude of effect of nutritional level 128 where the magnitude is related to daily, weekly, monthly, and the like, recommended nutrient amounts. Such nutritional level 128 may be used to determine target nutrient amounts with the goal of addressing hematological disorder, wherein the nutritional level 128 is a feasible amount that the subject may consume within the determined schedule. Persons skilled in the art, upon receiving the benefit of this disclosure in its entirety, may appreciate that hematologic model 136 may determine increasingly complicated relationships between 100+ different nutrient types and the many hematological disorder bundles 120 subjects may be assigned.

Continuing in reference to FIG. 1, identifying nutritional level 128 may include determining a respective effect of each nutrient of a plurality of nutritional levels on the hematological disorder bundle 120. An "effect of a nutrient," as used in this disclosure, is a change, consequence, and/or result in at least a hematological datum 108, hematological profile 112, and/or hematological disorder bundle 120 due to consumption of an amount of a nutrient. A "nutrient amount," as used in this disclosure, is a numerical value(s) relating to a nutrient level 128. Nutrient amount may include mass amounts of a vitamin, mineral, macronutrient (carbohydrate, protein, fat), a numerical value of calories, amounts of phytonutrients, antioxidants, probiotics, nutraceuticals, bioactive ingredients, and the like. An effect of a nutrient amount may include "no effect", "negligible effect", and/or "no calculated effect". Determining an effect of a nutrient may include determining how a hematological datum 108 may change, such as an increase/decrease according to a particular amount of nutrient. For instance and without limitation, such a determination may include calculating the effect of chronic, sustained nutrient amounts in a diet for weeks and/or months on epigenetic factors, blood serum levels of biomarkers, and the like.

Continuing in reference to FIG. 1, determining a respective effect of each nutrient amount of the plurality of nutrients may include retrieving the effects of the nutrient amount on the hematological disorder bundle 120. Computing device 104 may search for a nutrient effect using each hematological datum 108, and/or combination thereof contributing to the disorder, to locate and retrieve effects correlated to nutrients targeting a hematological datum 108. Retrieving an effect of a nutrient may include retrieving a hypothesis about the outcome for a subject after consuming a nutrient amount and/or amount of a combination of nutrients. Such a hypothesis may include an equation, function, among other mathematical forms, for instance derived from empirical relationships between a nutrient and the physiological integrity of an organ, biological system, and the like. Retrieving an effect may include retrieving from a database, a research repository, or the like. Retrieving an effect may include, for instance, searching using the hematological profile 112, a web browser, and the Internet, for a plurality of effects that nutrients may have. Retrieving an effect may include searching using the hematological disorder bundle 120 for an effect of a nutrient. In some embodiments, retrieving an effect may include calculating at least an effect, for instance by deriving a function from training data using a machine-learning algorithm.

Continuing in reference to FIG. 1, in non-limiting illustrative examples, determining an effect of a nutrient may include calculating if a change in hematological disorder bundle 120 may arise from adding and/or removing a nutrient from a subject's diet. For instance and without limitation, changing a hematological disorder bundle 120 from "severe anemia" to "normal serum iron level" with increasing dietary heme-based iron from animal products by introducing nutrition elements 140, such as beef, pork, chicken, veal, fish, and the like. Calculating an effect of a nutrient may include a mathematical operation, such as subtraction, addition, and the like. Calculating an effect of a nutrient may include retrieving an empirical equation that describes relationships between a nutrient and hematological datum 108, test results, hematological parameter, and the like. Calculating an effect of a nutrient may include deriving an algorithm, function, or the like, for instance using a machine-learning process and/or model. Calculating such an effect using machine-learning may include training data that includes a plurality of nutrients as it relates to effects on hematological data 108 and/or hematological disorder bundle 120.

Continuing in reference to FIG. 1, determining a respective effect of each nutrient amount of the plurality of nutrients may include generating a machine-learning model. Training data may include nutrient amounts correlated to their effect on the human body. For instance and without limitation, supplementation of amounts of fat-soluble vitamins, water-soluble vitamins, trace elements, minerals, electrolytes, among other nutrient categories in the diet may be correlated to renal function, liver function, vision integrity, bone mineral density, and the like. Such training data may originate from a database, research repository, clinical data, physician, plurality of subjects, or any other source described herein. Computing device 104 may generate a machine-learning model with such training data to derive an equation and/or function which describes relationships observed in the training data. Computing device 104 may then automatedly derive a respective effect for each nutrient, or nutrient combination, wherein the effect may become increasingly defined by parameters relating to the type of hematological disorder in the subject. The effect may also be related to an equation wherein, the magnitude of effect may be determined for all amounts of the nutrient. In this way, a particular nutrient amount may be determined based on the magnitude of effect desired.

Continuing in reference to FIG. 1, calculating a plurality of nutrient amounts may include generating training data using a plurality of predicted effects of the plurality of nutrient amounts. Training data may include retrieving effects on hematological function for nutrients. Computing device 104 may generate training data which includes nutrient amounts correlated to hematological disorder bundle 120 the nutrient is intended to target by retrieving effects and linking data elements to one another and storing in a database. Training data may include nutrient identities correlated to particular disorders, for instance vitamin B12, copper, and vitamin C deficiency may correlate to cytopenia and hematologic symptoms. Training data may include nutrient combinations from peer-reviewed studies correlated to hematologic symptoms, for instance combination supplementation of folate, vitamin B12, and methylmalonic acid (MMA) may address hematologic symptoms specifically in subjects adhering to strict ovo-vegetarian diets. Training data may include identified nutrient deficiencies in cohorts of subjects with particular lifestyle indicators, diet types, pre-existing conditions, co-morbidities, and the like. Training data may include nutrient surpluses in cohorts of subjects with no hematological disorder to compare against in identifying novel nutrients and combinations which may prevent hematologic symptomology. Training data may originate from any source described herein, for instance and without limitation, from a physician, via subject input from a plurality of subjects, a database, as described in further detail below, research repository, wearable device, physiological sensor, and the like.

Continuing in reference to FIG. 1, calculating the plurality of nutrient amounts may include generating a machine-learning model according to the training data, wherein training data includes a plurality of data entries that correlates the magnitude of nutrient effect to a plurality of nutrient amounts for each hematological disorder bundle 120. Such a machine-learning model may include any machine-learning process, algorithm, and/or model as performed by machine-learning module described in further detail below. The machine-learning model may be trained with training data that includes a plurality of data entries that includes nutrient effects, including the magnitude of effect, and effects of nutrient combination correlated to hematological disorder bundle 120. Data may be correlated to hematological disorder bundle 120 in that it is correlated to particular hematological data 108, symptom alleviation, may be found in a subset of healthy adults, among other correlations. In this way, such a machine-learning model may derive equations, functions, among other heuristics, which describe relationships observed in the training data regarding the full spectrum of nutrient amounts targeted to the subject's hematological disorder bundle 120 and/or hematological data 108.

Continuing in reference to FIG. 1, computing device 104 may calculate nutrient amounts, for instance, by retrieving a default amount from a database. Computing device 104 may retrieve standard nutrient amounts, such as from a standard 2,000 calorie diet, and alter the amount according to a numerical scale associated with hematological data 108 in the hematological profile 112. Such a calculation may include a mathematical expressing using operations such as subtraction, addition, multiplication, and the like, for instance an equation that assigns a variable to the subject's body weight, hematological parameters summarized in hematological profile 112, and retrieve a default value of a vitamin and alter the amount using the mathematical expression. Alternatively or additionally, such a calculation may involve deriving a loss function, vector analysis, linear algebra, system of questions, among other mathematical heuristics, depending on the granularity of the process. Deriving such a process for calculating nutrient amounts may include machine-learning, as described herein. Nutrient amounts may include threshold values, or ranges of values, for instance and without limitation, between 80-120 mg vitamin C per 24 hours, wherein the range changes as a function of hematological profile 112. Nutrient amounts may be calculated as heat maps (or similar mathematical arrangements), for instance using banding, where each datum of hematological profile 112 elicits a particular nutritional level 128 of a particular nutrient amount or set of amounts. In non-limiting illustrative examples, such a calculation may include querying for and retrieving a standard amount of water soluble vitamins for a healthy adult, for instance as described below in Table 1:

TABLE 1

| Nutrient | Amount |
| --- | --- |
| Vitamin C | 60 mg/day |
| Thiamin (B1) | 0.5 mg/1,000 kcal; 1.0 mg/day |
| Riboflavin (B2) | 0.6 mg/1,000 kcal; 1.2 mg/day |
| Niacin (B3) | 6.6 NE/1,000 kcal; 13 ND/day |
| Vitamin B6 | 0.02 mg/1 g protein; 2.2 mg/day |
| Vitamin B12 | 3 μg/day |
| Folic Acid | 400 μg/day |

Continuing in reference to FIG. 1, in reference to Table 1 above, wherein NE is niacin equivalent (1 mg niacin, or 60 mg tryptophan), mg (milligram), kcal (1000 kcal=1 Calorie), and μg (microgram). Computing device 104 may store and/or retrieve the above standard nutrient amounts, for instance via a database. The amounts may be re-calculated and converted according to a subject's hematological profile 112. For instance, these amounts may relate to an average BMI, healthy adult male, for any range of calories, but may be adjusted according to unique subject-specific hematological data 108. In non-limiting illustrative examples, a geriatric woman who adheres to a 1,400 Calorie/day diet, with complete blood count (CBC) test results indicating decreased WBC, RBC, and hemoglobin concentration, may be provided custom target nutrient values that deviate from the default values. In such an example, nutrient amounts may be curated according to the identified risk factors (hematological data 108) and the above nutrient amounts may be recalculated, where some amounts may increase, some may decrease, and some may remain constant.

Continuing in reference to FIG. 1, calculating nutrient amounts may include deriving a weighting factor to adjust, or otherwise re-calculate, an amount. Weighting factor may be determined by computing device 104, for instance, by querying for vitamin amounts according to data inputs identified in the hematological profile 112. For instance in non-limiting illustrative examples, if hematological profile 112 indicates decreased energy, pancytopenia, failure to thrive, and hypotonia. Management of coagulopathy may include treatments such as fresh frozen plasma, pRBC, platelet transfusions, and vitamin K supplementation. In such an instance, further diagnostic testing may reveal markedly low serum B12 with elevated MMA and homocysteine levels, mildly low folate and copper levels, and markedly low vitamin D level. Pancytopenia and coagulopathy may improve in as soon as within 7 days on oral vitamin K, 2 doses of vitamin B12, vitamin ADEK, and copper. In such a symptomology manifestation, issues may be found to be due to milk protein allergy. Therefore, standard predetermined diets which may increase protein or suggest animal products may have worsened the condition due to elevated MMA, homocysteine, and milk protein allergy. The consumption schedule for the individual may be altered such that the subject is weaned off oral vitamin K, vitamin ADEK, copper, and vitamin B12 supplementation once hematological data 108 indicate normal CBC. In such an instance, relationships may be identified in nutrient amounts relating to addressing the hematological disorder bundle 120 of such an individual, specifically in supplementing the diet with specific foods items rich in those vitamins and minerals, whereas it may be inversely associated with consumption of certain animal products such as red meat and/or dairy products. Additionally, vitamins found in such foods from organic sources may be superior from nonorganic sources, such as from commercially-available supplements, from a bioavailability standpoint. Per-subject pharmacokinetics, rates of metabolism and/or adsorption of nutrients may differ subject-to-subject, which may negate the effectiveness of proscribing particular predetermined diet types and nutrition elements 140 to subjects. In such an instance, computing device 104 may account for such details using machine-learning to derive more specific nutrient amount calculations and to more accurately calculate the amounts by which to increase/decrease nutrients found in such foods as evidence by the presence of hematological data 108. Therefore, computing device 104 may derive weighting factors to account for particular genotype, phenotype, epigenetic factors, organic vs non-organic sources, and the nutrition element types with which the nutrients may originate.

Continuing in reference to FIG. 1, in non-limiting illustrative examples, computing device 104 may use a machine-learning process to perform a machine-learning algorithm to derive per-subject pharmacokinetics, for instance of vitamin B6. The machine-learning algorithm may accept an input of numerical values including the total amount of protein consumed (in grams), total amount of vitamin B6 consumed (in mg) per day in a diet, and serum levels of the vitamin B6 vitamer, pyridoxal-5-phosphate, over the course of a month, and derive the rates of metabolism, or how 'well' the subject is obtaining the vitamin from nutrition elements 140 and adsorbing vitamin B6. In other words, the algorithm may derive a function such as using linear regression, vector quantization, least squares, among other algorithms, that describes the pharmacokinetics for that particular subject regarding what amount of vitamin B6 consumed, per amount of dietary protein, results in what corresponding amount of bioactive vitamin compound, as measured by the blood vitamer from a biological extraction. Such a function, derived from machine-learning, may then be used by computing device 104 with an input of the hematological profile 112, which enumerates hematological data 108, to calculate an output which is a more accurate, customized, per-subject nutrient amount of vitamin B6. Persons skilled in the art, upon benefit of this disclosure in its entirety, may appreciate that this process may be repeated for the full spectrum of nutrients, both required as part of a diet and not required as part of a diet, to control for specific metabolic differences in a population. Alternatively or additionally, such a process may identify new gut malabsorption issues related to nutrients that are recommended but not typically associated with disease.

Continuing in reference to FIG. 1, additionally, in non-limiting illustrative examples, computing device 104 may relate the concentrations of the metabolic products related to vitamins (e.g. vitamers), minerals, phytonutrients, probiotics, antioxidative compounds, biologically active ingredients, prodrugs, and the like, to their effective concentrations in tissues. For instance, computing device 104 may additionally search and retrieve data that relates the blood levels of the vitamin B6 vitamer, pyridoxal-5-phosphate, to the effective concentrations of vitamin B6 in the liver, which is particularly sensitive to aberrations in hematologic function. Computing device 104 may store and/or retrieve values in a "look-up table", or graph a relationship as a mathematical function, among other ways of representing a data structure that relates the data identified in the search. Alternatively or additionally, computing device 104 may derive a function, for instance using machine-learning, which correlates the concentration of a compound in a particular biological extraction, such as blood, to varying amounts in tissues such as breast tissue, liver, kidneys, and the like This may prove helpful in calculating nutrient amounts as a function of subject consumption to specific target nutrient amount quantities within a particular organ/tissue according to the input data in the hematological profile 112.

Continuing in reference to FIG. 1, computing device 104 may determine nutrient amounts by receiving input from the subject and calculating nutrition inputs. "Nutritional input," as used in this disclosure, is an amount of a nutrient consumed by a subject. Nutritional input may be received and/or calculated, for instance and without limitation, as described in Ser. No. 16/911,994, filed Jun. 25, 2020, titled "METHODS AND SYSTEMS FOR ADDITIVE MANUFACTURING OF NUTRITIONAL SUPPLEMENT SERVINGS," the entirety of which is incorporated herein by reference. Computing device 104 may receive nutritional input from subject. Nutritional input, for instance and without limitation, may include food items that have associated nutrition facts, wherein computing device 104 may calculate, weight, or otherwise modify, the nutritional input from the subject, such as with a weighting factor. This results in accurate, per-subject nutritional input. Such nutritional input may be used to determine target nutritional level 128. For instance and without limitation, if subject regularly consumes <2,000 calorie diets due to elevated visceral fat content, hip-to-waist-ration, and increased body mass index (BMI), hematologic model 136 may determine nutritional levels 128 that may address hematological disorder bundle 120 and is feasible within the daily target calorie level.

Continuing in reference to FIG. 1, computing device 104 is configured to identify, using the at least a nutritional level 128, at least a nutrition element. A "nutrition element," as used in this disclosure, is an item that includes a nutrient amount intended to be consumed by subject. Nutrition element 140 may include alimentary elements, such as meals (e.g. chicken parmesan with Greek salad and iced tea), food items (e.g. French fries), grocery items (e.g. broccoli), health supplements (e.g. whey protein and multivitamin), beverages (e.g. orange juice), and the like. Nutrition element 140 may be "personalized" in that nutrition elements are curated in a guided manner according to hematological data 108, hematological profile 112, hematological disorder bundle 120, subject-designated symptoms, food allergies and/or intolerances, subject preferences, and the like. Nutrition element 140 may include a specific dietary category, such as a "ketogenic diet", "low glycemic index diet", "Paleo diet", among others. Nutrition element 140 may include custom meals, recipes, and/or beverage which may not be traditionally found, such as a "health shake" which includes a unique, proprietary blend of ingredients that is optimized for a particular subject.

Continuing in reference to FIG. 1, identifying the at least a nutrition element 140 may include generating a nutrition model training data including a plurality of data entries of levels correlating to nutrition elements, and determining at least a nutrition element 140 as a function of the nutrition model and at least a nutritional level 128. Nutrition model may be generated using a nutrition machine-learning process including any machine-learning algorithm, process, and/or model as performed by a machine-learning module, as described in further detail below. Nutrition model 144 may be trained using training data which originates from any source, as described herein, for instance and without limitation retrieved from a database, retrieved via a web browser and the Internet, peer-reviewed research repository, clinical data, subject input data, wearable device, physiological sensor, medical history data, and the like. Training data may include a plurality of data entries including ranges of values of nutrients, for a variety of nutrient types and classes such as water-soluble vitamins, fat-soluble vitamins, transition metal nutrients, trace metals, alkali earth metal nutrients, phytonutrients, essential amino acids, and the like, which are related to nutrition elements that contain varying amounts of each. Such training data may be used to determine which to mix-and-match into combinations to arrive at which nutrition elements should be consumed within particular ranges of time (within a meal, a day, week, and the like) to arrive at target nutritional level 128. Training data may be segmented by cohort, where nutritional level 128 for large sets (>1,000+) of healthy subjects is compared to nutritional levels of cohorts of subjects classified by hematological disorder bundle 120 to calculate nutrition elements 140 which may close the gap between the cohorts.

Continuing in reference to FIG. 1, computing device 104 may determine the at least a nutrition element 140 as a function of the nutrition machine-learning process and the at least a nutritional level 128. Nutrition model 144 may be trained to derive mathematical relationships observed in the training data to automatedly accept nutritional level 128 inputs and calculate an output that is at least a nutrition element 140, of a plurality of nutrition elements 140. Nutrition element 140 outputs may include sets, or combinations, of nutrition elements that are categorized as packets necessary to reach nutrient targets. For instance and without limitation, nutrition elements may include at least one element from a "fruit" category, "vegetable" category, and "grain category", that may be arranged such that a meal will achieve at least a first nutritional level 128, without over-contributing to a second nutritional level 128. Nutrition model 144 may determine an amount of nutrition element 140 where the amount is related to how much should be consumed in a meal, day, week, and the like. Persons skilled in the art, upon receiving the benefit of this disclosure in its entirety, may appreciate that nutrition model 144 may identify thousands or more nutrition elements for each hematological disorder bundle 120 that should be avoided or included into a diet according to any number of nutritional levels 128.

Continuing in reference to FIG. 1, identifying at least a nutrition element 140 may include retrieving a plurality of nutrition elements 140 from a data repository as a function of at least a nutritional level 128. Data repository may include any data structure including and/or suitable for use as a hematological program database, as described in further detail below. Identifying a plurality of nutrition elements 140 may include retrieving nutrition elements that correspond to a nutritional level 128 of the plurality of nutrient amounts, according to data present in hematological profile 112. For instance and without limitation, hematological parameters that indicate nutrition-linked hematological disorder bundle may result in retrieval of nutrition elements 140 that contain a minimal nutrient content according to hematological relationship 132. Computing device 104 may accept an input of at least a nutritional level 128 and retrieve nutrition elements 140 by searching a database for nutrition elements according to the nutrient and its range of values. Computing device 104 may accept an input of nutritional level 128 and may search using a web browser and the Internet for nutrition elements 140 according to the nutrient and its amount.

Continuing in reference to FIG. 1, identifying the plurality of nutrition elements 140 may include identifying the nutrition elements 140 according to the hematological disorder bundle 120. Computing device 104 may accept an input of a hematological disorder bundle and retrieve a nutrition element 140, or category of nutrition elements according to the classification. Identifying nutrition element 140 according to hematological disorder bundle 120 may include querying, for instance using a web browser and the Internet, for foods, supplements, bioactive ingredients, and the like, which are correlated with a particular hematological disorder bundle 120. For instance and without limitation, computing device 104 may organize a search for foods intended for "low platelet concentration", wherein an entire diet may be crafted around target nutritional levels 128 and the categorization of the hematological profile 112 to a hematological disorder bundle 120 that relates to the need for increasing platelets. In such an example, the nutrition elements 140 are outputs generated from an input search criteria of "low platelet concentration" and its associated nutritional levels 128. The output elements become "personalized" as they are arranged into daily, weekly, monthly, and the like, individual meals and/or consumption schedule according to a subject's particular calculated nutrient amounts. The hematological disorder bundle 120 may serve as a filtering step, wherein a search is guided by the hematological profile 112 as it was classified to a disorder type.

Continuing in reference to FIG. 1, identifying the plurality of nutrition elements 140 may include generating combinations of located nutrition elements as a function of fulfilling the plurality of nutrient amounts. In this way, custom meals may be generated according to the nutritional needs calculated of a hematological disorder. Computing device 104 may identify the plurality of nutrition elements 140 by using nutritional level 128 as an input and generating combinations, lists, or other aggregates of nutrition elements 140 necessary to achieve nutritional level 128. For instance, computing device 104 may use a template nutritional level 128 of '200 mg vitamin C' and build a catalogue of nutrition elements 140 until the 200 mg vitamin C value is obtained. Computing device 104 may perform this task by querying for food items, for instance from a menu, grocery list, or the like, retrieving the vitamin C content, and subtracting the value from the nutritional level 128. In non-limiting illustrative examples, computing device 104 may identify orange juice (90 mg vitamin C/serving; 200 mg-90 mg=110 mg) for breakfast, Brussel sprouts (50 mg vitamin C/serving; 110 mg-50 mg=60 mg) for lunch, and baked potato (20 mg vitamin C/serving) and spicy lentil curry (40 mg vitamin C/serving; 60 mg-(20 mg+40 mg)=0 mg) for dinner. In such an example, computing device 104 may search according to a set of instructions such as subject preferences, allergies, dietary restrictions, and the like, provided by a physician, medical history, subject input, among other sources, and subtract each identified nutrition element 140 nutrient from nutritional level 128 until a combination of nutrition elements 140 that represents a solution is identified. Once a solution is found, computing device 104 may generate a file of nutrition elements 140 and store in a database, as described in further detail below. In this way, computing device 104 may generate customized meals, health shakes, recipes, and the like, which may be retrieved from a database as identified for a first subject and provide to a second subject which has been classified to a similar hematological disorder bundle 120.

Continuing in reference to FIG. 1, computing device 104 is configured to generate a hematological program using the at least a nutrition element, wherein the hematological program includes a consumption program. A "hematological program," as used in this disclosure, is a collection of nutrient amounts and nutrition elements 140 for addressing hematological disorder. Hematological program 148 may include meals organized into a consumption program. A "consumption program," as used in this disclosure, is a frequency and magnitude associated with at least a nutrition element 140. A "frequency," as used in this disclosure, is a number of consumption occurrences associated with a time course, such as daily, weekly, monthly, and the like, of which a nutrition element 140 is intended to be consumed. Frequency may be determined as a function of the identified effect, wherein the frequency of consumption is tailored to provide a sufficient minimal nutritional level 128 over a period. A "magnitude," as used in this disclosure, is a serving size of at least a nutrition element 140 as a function of the identified effect. Identifying the magnitude associated with a nutrition element may include calculating a serving size of the at least a nutrition element as a function of the identified effect, where the serving size may be divided into quantities to be consumed according to a frequency. Hematological program 148 may include gathering, classifying, or otherwise categorizing nutrient amounts and/or nutrition elements 140 lists, which incorporates hematologic-specific recommendations. For instance, nutrition elements 140 may be scored with a numerical score scale that associates a meal, beverage, supplement, and the like, with addressing hematological disorder, alleviating symptoms, and the like. Hematological program 148 may include selecting nutrition elements 140 according to a threshold score, where items above the threshold are selected and arranged into meals. Threshold score may include a daily threshold, wherein nutrition elements 140 are selected each day according to the threshold; and threshold may include a numerical value relating to symptom prevention, a calculated nutrient amount, among other outputs of system 100 described herein. Determining hematological program 148 may include machine-learning. For instance and without limitation, training a machine-learning model to identify a scoring rubric for building the hematological program 148 based on some criteria such as preventing biomarkers from increasing/decreasing, alleviating symptoms, among other criteria. Hematological program 148 may relate specific hematological disorder bundle 120 to specific nutrients of interest and provide nutrition element 140 scheduling times and serving sizes for each meal according to the categorization. Hematological program 148 may differ from one subject to the next according to the magnitude of the disease outline (hematological disorder bundle 120 and hematological profile 112).

Continuing in reference to FIG. 1, generating the hematological program may include receiving a subject preference. A "subject preference", as used in this disclosure, is a user input that designates a preference related to at least a nutrition element 140. Subject preference may include designations of nutrition elements 140 to avoid and/or include such as particular food groups, ingredients, condiments, spices, dietary restrictions such as 'no animal products', cuisine type such as 'Mediterranean foods', time of day for eating such as 'fasting before 10 am', and the like. Subject preference may include indications of allergies, food intolerances, and the like, which may represent constraints on curating nutrition elements 140. In this way, computing device 104 may accept an input of subject preference filter, sort, classify, or otherwise modify the data structure of nutrition elements 140 and schedule the nutrition elements 140 into hematological program 148 in a custom, per-subject manner. Computing device 104 may modify the plurality of nutrition elements 140 as a function of the subject preference, for instance by providing recipes with steps omitted, new steps added, or entirely new recipes altogether utilizing the same or different nutrition elements 140. Computing device 104 may modify the plurality of nutrition elements 140 as a function of the subject preference by generating a new file, based on the preference, and storing and/or retrieving the file from a database, as described in further detail below.

Continuing in reference to FIG. 1, generating the hematological program 148 may include generating a linear programming function with the plurality of nutrition elements wherein the linear programming function outputs at least an ordering of plurality of nutrition elements according to the nutritional level 128. An "linear programming function," as used in this disclosure, is a mathematical objective function that may be used by computing device 104 to score each possible combination of nutrition elements 140, wherein the linear programming function may refer to any mathematical optimization (mathematical programming) to select the 'best' element from a set of available alternatives. Selecting the 'best' element from a set of available alternatives may include a combination of nutrition elements 140 which achieves the nutrient amounts in addressing hematological disorder in a subject. Alternatively or additionally, linear programming function may generate solutions according to constraints placed by subject preferences.

Still referring to FIG. 1, linear programming function may be formulated as a linear program, which computing device 104 may solve using a linear program, such as without limitation, a mixed-integer program. A "linear program," as used in this disclosure, is a program that optimizes a linear programming function, given at least a constraint; a linear program may be referred to without limitation as a "linear optimization" process and/or algorithm. For instance, in non-limiting illustrative examples, a given constraint might be a metabolic disorder of a subject, as indicated by Subject preference, and a linear program may use a linear programming function to calculate combinations, considering how these limitations effect combinations. In various embodiments, system 100 may determine a set of instructions towards addressing a subject's hematological profile 112 that maximizes a total hematological disorder prevention score subject to a constraint that there are other competing objectives. For instance, if achieving one nutritional level 128 by selecting from a first nutrition element 140 may result in needing to select a second nutrition element 140, wherein each may compete in degradation prevention (e.g. adopting two or more diet types simultaneously may not be feasible, a vegan option and a non-vegan option, and the like). A mathematical solver may be implemented to solve for the set of instructions that maximizes scores; mathematical solver may be implemented on computing device 104 and/or another device in system 100, and/or may be implemented on third-party solver.

Continuing in reference to FIG. 1, implementation of a linear programming function may include performing a greedy algorithm process. A "greedy algorithm" is defined as an algorithm that selects locally optimal choices, which may or may not generate a globally optimal solution. For instance, computing device 104 may select combinations of nutrition elements 140 so that values associated therewith are the best value for each category. For instance, in non-limiting illustrative example, optimization may determine the combination of the most efficacious 'magnitude', 'frequency', 'nutrition-linked hematological disorder bundle', 'nutrition-linked disorder prevention bundle', 'probiotic', 'vegetable', 'nutrient amount per meal', among other categories to provide a combination that may include several locally optimal solutions but may or may not be globally optimal in combination.

With continued reference to FIG. 1, linear programming function may include minimizing a loss function, where a "loss function" is an expression of an output of which a process minimizes to generate an optimal result. For instance, achieving nutritional levels 128 may be set to a nominal value, such as '100', wherein the linear programming function selects elements in combination that reduce the value to '0', wherein the nutrient amounts are '100% achieved'. In such an example, 'maximizing' would be selecting the combination of nutrition elements 140 that results in achieving nutrient amounts by minimizing the difference. As a non-limiting example, computing device 104 may assign variables relating to a set of parameters, which may correspond to hematologic symptom prevention components, calculate an output of mathematical expression using the variables, and select an objective that produces an output having the lowest size, according to a given definition of "size." Selection of different loss functions may result in identification of different potential combinations as generating minimal outputs, and thus 'maximizing' efficacy of the combination.

Continuing in reference to FIG. 1, computing device 104 may use calculated nutrient amounts from hematologic model 136 to determine nutrition elements 140 more precisely. For instance, computing device 104 may retrieve a variety of nutrition elements 140 which contain particular vitamins, minerals, anti-inflammatory molecules, phytonutrients, antioxidants, bioactive molecules, and the like, which do not violate any other hematologic prevention information associated with hematological profile 112. Computing device 104 may mix-and-match nutrition elements 140 to arrive at a particular calorie amount, range of calories, or number of macromolecules, while achieving nutrient amounts. In this way, de novo nutrition element 140 that may not exist may be created from various ingredients according to their nutrient profile.

Continuing in reference to FIG. 1, generating the hematological program 148 may include generating a hematological program classifier using a hematological program classification machine-learning process to classify nutrition elements 140 according to hematological symptom and/or disorder, and outputting a plurality of nutrition elements as a function of the hematological program classifier. Hematological program classifier may include any classifier, as described herein, generated by a classification machine-learning process using training data, performed by a machine-learning module as described in further detail below. Training data for hematological program classifier may include sets of data entries that include nutrition elements 140 that are correlated to hematological categories relating to symptoms, biomarkers, and disorders. Classifier may be trained to automatedly locate, sort, and output nutrition elements 140 according to calculated nutrient amounts for the subject belonging to such a categorization. Such training data may originate via a database, the Internet, research repository, and the like, as described herein for training data for other machine-learning processes. Training data may include foods, supplements, probiotics, nutraceuticals, and the like, correlated to nutrition facts, medicinal qualities, and the like, which a classifier may be trained to identify relationships that aid in sorting nutrition elements 140 according to a relationship to a disorder. Hematological program classifier may accept an input of hematological disorder bundle 120 and output a plurality of nutrition elements 140 with associated consumption program according to relationships identified in training data. For instance and without limitation, hematological program classifier may identify relationships between individual fruits and vegetables, that when more vegetables are selected, certain fruits may not be necessary to schedule within the same timeframe. Such a classification process may determine a function, system of equations, and the like, which can be solved for in determining which nutrition elements 140 are useful toward obtaining the nutrient amounts, while not missing some lower limits of nutrient amounts (trace elements) and not exceeding upper limits for other nutrient amounts (calories).

Continuing in reference to FIG. 1, hematological program 148 may include a hematological score. A "hematological score," as used in this disclosure, is a quantitative datum representing a level of subject participation in hematological program 148 and/or a level of hematological disorder in the subject as a function of adherence to hematological program 148. Hematological score 152 may include a numerical value, metric, parameter, and the like, described by a function, vector, matrix, or any other mathematical arrangement. Hematological score 152 may include enumerating a subject's current nourishment as it relates to symptoms alleviation, increased/decrease biomarker levels and/or concentrations, and/or hematological disorder prevention. Generating hematological score 152 may include using a machine-learning process, algorithm, and/or model to derive a numerical scale along which to provide a numerical value according to a subject's hematological profile 112 and participation in hematological program 148 generated from hematological profile 112. For instance, such a machine-learning model may be trained with training data, wherein training data contains data entries of nutrient amounts correlated to hematological disorder prevention. Such a machine-learning model may be trained with said training data to be used by computing device 104 to correlate the consumption of particular nutrition elements 140 in hematological program 148 to achieving some nutritional level 128, and how nutritional level 128 relates to symptom alleviation, and the like. Training data for a machine-learning model for generating hematological score 152 may include a plurality of data entries including nutrient amounts correlated to effects on hematological function, wherein the trained model may accept inputs of nutritional input from subject and automatedly determine how the score should increase and/or decrease based on the nutrient targets for the subject. Such training data may originate from any source as descried above, such as a database, web browser and the Internet, physician, peer-reviewed research, and the like.

Continuing in reference to FIG. 1, in non-limiting illustrating examples, falling short of copper and B-complex vitamin nutrient amounts, may have a particular effect on hematological score 152 for an individual who has been classified to a certain hematological disorder bundle 120. Where, chronically falling short of the nutrient amount results in a (−3) score each month but falling within the nutrient amount range affords (+1) score for each month; the target amount for the preceding month may dictate the score change for each subsequent month. In such a case, a machine-learning model may derive an algorithm which dictates the amount to increase/decrease hematological score 152 for that particular hematological disorder bundle 120 according to the nutrient amounts. In this case, the machine-learning model is trained to identify the relationship between nutrient amounts and effect on score to derive an equation that relates scoring criteria to nutritional input. The score is then calculated using the model and nutritional input from the subject. In this way, computing device 104 may calculate a hematological score 152 as a function of a subject's participation in Hematological program 148, where hematological score 152 is updated with each nutrition element 140 consumed by subject.

In an embodiment, and as a non-limiting illustration, classification of a subject to a hematological disorder bundle as a function of their blood biomarker data may include a predictive diagnosis pertaining to the subject as a function of their hematological profile. Such classification may include: 1) diagnosis based on comparison to a subject cohort, and/or 2) diagnosis based on comparison to normalized thresholds, as the cohort may be susceptible to undiagnosed disorders. This may require: 1) retrieving a hematological profile, 2) determining a threshold value, 3) comparing the hematological profile to the threshold value, and 4) classifying subject to a hematological disorder bundle as a function of the comparison. The assignment of subject to hematological disorder bundle may be used to derive nutritional levels. The nutritional levels may be calculated as a function of relationships between blood biomarkers in the hematological profile and effects of nutrients on the blood biomarkers as it contributes to the hematological disorder bundle. Daily nutritional levels may then be used as an input to generate an output of food recommendations (may include querying via the Internet for nutrition elements and classification by hematological category). Nutrition recommendations may be assigned a score relating to their effect on the hematological disorder the subject was categorized to. Nutrition elements may be arranged using a linear programming function into daily, weekly, monthly consumption programs focused around addressing the hematological disorder according to constraints arising from user input. Addressing hematological disorder with nutrition may include prevention of future hematological disorder, reducing risk, and the like.

Continuing in reference to FIG. 1, in non-limiting exemplary embodiments, a differentiating factor may be found in the concept that a compendium of subject data may be used to classify subjects according to subsets of subjects based on biological extraction data. Subjects may be assigned predetermined diets or custom, de novo diets that are generated based on two factors: 1) assigning subjects to diet types and/or nutrient amounts according to how they classify to cohorts of alike subjects. For instance, if the subject's blood data indicates a pre-diabetic state, the subject may be assigned to what other pre-diabetic subjects have been assigned. And 2) outcomes associated with subject data. For instance, subjects with insulin insensitivity may have improved health outcomes associated with a particular nutritional level which was found effective in controlling blood glucose levels. The subject may be assigned a custom diet focused on this paradigm as a result of their blood data relating to that subset of subjects. In this case, a variable may be assigned to each element of biological extraction data for each subject where such a variable is associated with some outcome relating to nutrient amounts. This process may be performed, without limitation, as described in U.S. Nonprovisional application Ser. No. 17/106,588, filed Nov. 30, 2020, titled "METHODS AND SYSTEMS FOR DETERMINING A PREDICTIVE INTERVENTION USING BIOMARKERS," the entirety of which is incorporated herein by reference.

Continuing in reference to FIG. 1, in non-limiting exemplary embodiments, machine-learning may identify relationships in training data (subsets of subject data—biological extraction and nutritional input data) which may be assigned variables to derive an algorithm, function, equation, and the like, which describes a nutritional level. Variables may be assigned values based on thresholds relating to the biomarker levels, for instance as found among cohorts of healthy adults. This way, population-based nutrigenomics may be employed to individual subjects who may be classified to consumption programs based on how they compare to entire populations of subjects. Such populations of subjects may be subsets that belong in a "goal category" relating to the subject. For instance, if the subject has a BMI of 35 and has a target goal of a BMI of 15-20, the target population used may be subjects within the goal BMI, including their corresponding biological extraction variables. The system may then calculate nutrient amounts and identify nutrition elements that will result in the subject's BMI reaching the goal population. This may require a nutrient-blood biomarker relationship (hematological relationship) to be derived among the population the subject belongs and the target population. Comparison between the population may identify biomarkers that are to address and potentially differences in diet that may address the difference.

Figure 2:
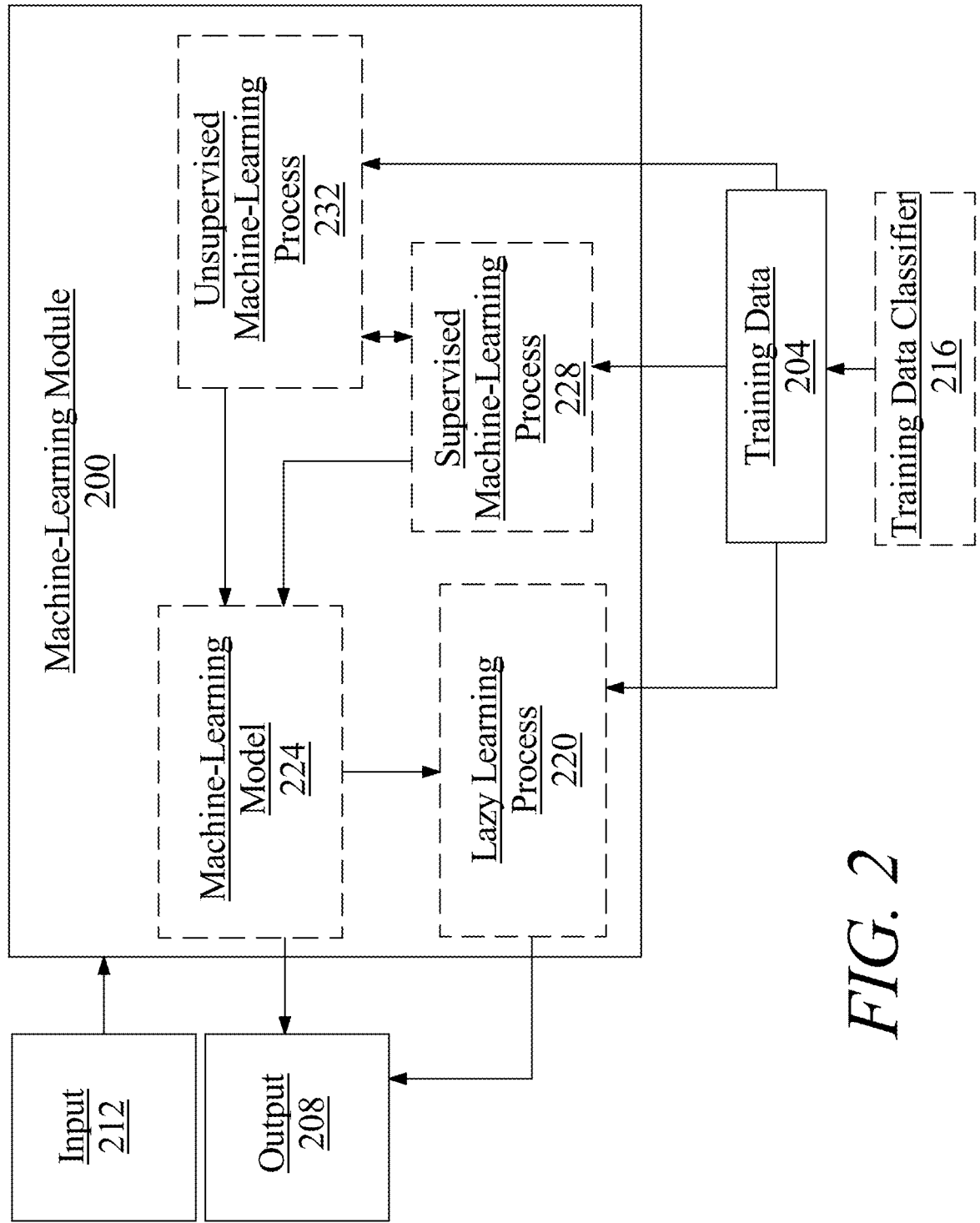
FIG. 2 is a block diagram illustrating a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a subject and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail herein. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail herein; such models may include without limitation a training data classifier 216. Training data classifier 216 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements that characterizes a sub-population, such as a subset of hematological data 108 and/or other analyzed items and/or phenomena for which a subset of training data may be selected.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements, such as classifying hematological datum 108 elements to hematological profile 112 elements and assigning a value as a function of some ranking association between elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used to derive numerical scales for providing numerical values to hematological profile 112 and/or hematological score 152, and the like, as described above, to "learn" the upper and lower limits to the numerical scale, the increments to providing scoring, and the criteria for increasing and decreasing elements encompassed in the hematological profile 112 and/or hematological score 152, and the like. A machine-learning model may be used to "learn" which elements of hematological data 108 have what effect on hematological profile 112, and which elements of hematological profile 112 are affected by particular nutrition elements 140 and the magnitude of effect, and the like. The magnitude of the effect may be enumerated and provided as part of system 100, where nutrition elements 140 are communicated to subject for their symptom alleviation properties.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a hematological profile 112 (potentially classified into hematological disorder bundles 120), as described above as inputs, nutrition element 140 outputs, and a ranking function representing a desired form of relationship to be detected between inputs and outputs; ranking function may, for instance, seek to maximize the probability that a given input (such as nutrient amounts) and/or combination of inputs is associated with a given output (hematological program 148 that incorporate nutrient elements 120 to achieve nutrient amounts that are 'best' for hematological disorder bundle 120) to minimize the probability that a given input is not associated with a given output, for instance finding the most frequency, magnitude, and what the nutrition elements 140 should be, and the like. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon the benefit of reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning process 232. An unsupervised machine-learning process 232, as used herein, is a process that derives inferences in datasets without regard to labels; as a result, an unsupervised machine-learning process 232 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
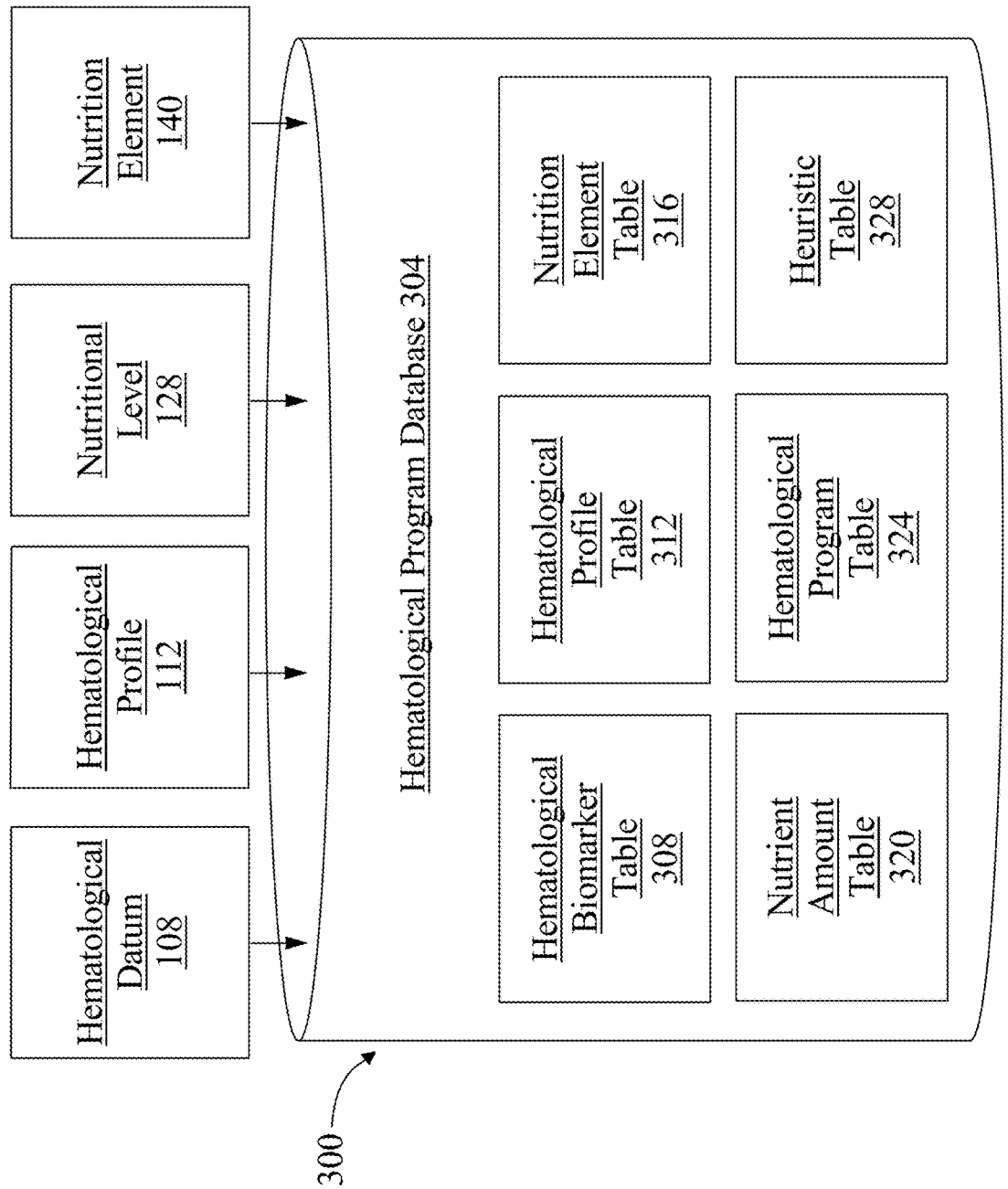
FIG. 3 is a block diagram of a hematological program database.

Referring now to FIG. 3, a non-limiting exemplary embodiment 300 of a hematological program database 304 is illustrated. Hematological datum(s) 108 from a plurality of subjects, for instance for generating a training data classifier 216, may be stored and/or retrieved in hematological program database 304. Hematological datum(s) 108 data from a plurality of subjects for generating training data 204 may also be stored and/or retrieved from a hematological program database 304. Computing device 104 may receive, store, and/or retrieve training data 204, wearable device data, physiological sensor data, biological extraction data, and the like, from hematological program database 304. Computing device 104 may store and/or retrieve nutrient machine-learning model 116, hematological classifier 124, among other determinations, I/O data, models, and the like, from hematological program database 304.

Continuing in reference to FIG. 3, hematological program database 304 may be implemented, without limitation, as a relational database, a key-value retrieval database such as a NOSQL database, or any other format or structure for use as a database that a person skilled in the art would recognize as suitable upon review of the entirety of this disclosure. Hematological program database 304 may alternatively or additionally be implemented using a distributed data storage protocol and/or data structure, such as a distributed hash table and the like. Hematological program database 304 may include a plurality of data entries and/or records, as described above. Data entries in a hematological program database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Further referring to FIG. 3, hematological program database 304 may include, without limitation, hematological datum table 308, hematological profile table 312, nutrition element table 316, nutrient amount table 320, hematological program table 324, and/or heuristic table 328. Determinations by a machine-learning process, machine-learning model, ranking function, and/or classifier, may also be stored and/or retrieved from the hematological program database 304. As a non-limiting example, hematological program database 304 may organize data according to one or more instruction tables. One or more hematological program database 304 tables may be linked to one another by, for instance in a non-limiting example, common column values. For instance, a common column between two tables of hematological program database 304 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 3, in a non-limiting embodiment, one or more tables of a hematological program database 304 may include, as a non-limiting example, a hematological datum table 308, which may include categorized identifying data, as described above, including hematological datum 108 data such as genetic data, epigenetic data, microbiome data, physiological data, biological extraction data, and the like. Hematological datum table 308 may include hematological datum 108 categories according to gene expression patterns, SNPs, mutations, enzyme specific activity and concentration, phosphorylation data, blood biomarker data, data concerning metabolism of nutrition elements 140, pharmacokinetics, nutrient absorption, and the like, and may include linked tables to mathematical expressions that describe the impact of each hematological datum 108 datum on hematological profile 112, for instance threshold values for gene expression levels of biomarkers, blood protein concentrations, WBC counts, and the like, as it relates to hematological parameters, hematological disorder bundle 120, and the like. One or more tables may include hematological profile table 312, which may include data regarding hematological datum 108, thresholds, scores, metrics, values, categorizations, and the like, that system 100 may use to calculate, derive, filter, retrieve and/or store current symptoms, formulas relating biomarkers to hematological parameters, biomarkers as they relate to hematological disorder bundle 120, and the like. One or more tables may include nutrition element table 316, which may include data on nutrition elements 140 for instance classified to hematological disorder bundle 120, classified to data from alike subjects with similar hematological datum 108, hematological profile 112, and the like, that system 100 may use to calculate, derive, filter, retrieve and/or store nutrition elements 140. One or more tables may include nutrient amount table 320, which may include functions, model, equations, algorithms, and the like, using to calculate or derive nutritional level 128 relating to hematological profile 112 and/or hematological disorder bundle 120, may include nutrient amounts organized by nutrient, nutrient classification, subject data such as age, sex, symptom severity, and the like. One of more tables may include a hematological program table 324, which may include nutrition element 140 identifiers, consumption programs, times associated with nutrition elements 140 regarding times to eat, identifiers of meals, recipes, ingredients, frequency, magnitude, diet types, and the like. One or more tables may include, without limitation, a heuristic table 328, which may organize rankings, scores, models, outcomes, functions, numerical values, scales, arrays, matrices, and the like, that represent determinations, probabilities, metrics, parameters, values, and the like, include one or more inputs describing potential mathematical relationships, as described herein.

Referring now to FIGS. 4A and 4B, a non-limiting exemplary embodiment 400 of a hematological profile 112 is illustrated. Hematological profile 112 may include a variety of hematological datum 108 categories, for instance 22 distinct categories, as shown in FIGS. 4A and 4B. Each hematological datum 108 may be assigned a value, such as an arbitrary value, where some hematological data 108, such as those shaded in light grey, may relate to absolute scales from [0, x], where x is a maximal value and the range of values for the hematological datum 108 cannot be below a 'zero amount'. Some hematological data 108, such as those shaded in dark grey, may relate to gene expression levels, wherein, the hematological datum 108 is enumerated as a 'box plot' that illustrates the range of concentrations of proteins, blood cell counts, hormone levels, and the like, in a population of subjects organized according to, for instance age, fitness level, nutrition, and the like. In such an example, the dashed line may relate to a 'normal threshold' above which the biomarker is considered elevated, below which is decreased. Each hematological datum 108 may have associated with it a numerical score, or some other identifying mathematical value that computing device 104 may assign. Persons skilled in the art, upon the benefit of this disclosure in its entirety, may appreciate that for each subject, any number of hematological data 108 may be enumerated and assigned a value according to hematological profile machine-learning model 116 and the breadth of biomarker data provided. Hematological profile 112 may be graphed, or otherwise displayed, according to the enumeration by hematological profile machine-learning model 116. Each bar of the bar graph, or combinations of bar graph categories, may instruct a classification of a subject's hematological profile 112 to a hematological disorder bundle 120.

Still referring now to FIGS. 4A and 4B, in non-limiting exemplary illustrations hematological profile 112 may be classified to a hematological disorder bundle 120. Some and/or all of the hematological data 108 summarized in hematological profile 112 may be used to classify an individual to a particular hematological disorder bundle 120. For instance, as shown in FIG. 4B, ten of the 22 hematological datum 108 categories may be used to classify hematological profile 112 to one or more hematological disorder bundles 120. Alternatively or additionally, hematological profile machine-learning model 116 may be trained to assign hematological datum 108 to a hematological disorder bundle 120, wherein computing device 104 may know the identity of hematological disorder bundle 120 according to which hematological disorder bundle 120 has the most identifying data points. Alternatively or additionally, hematological classifier 124 may be trained to assign subject to a hematological disorder bundle 120 according to patterns observed in hematological profile 112, for instance according to data from a subset of subjects.

Figure 5:
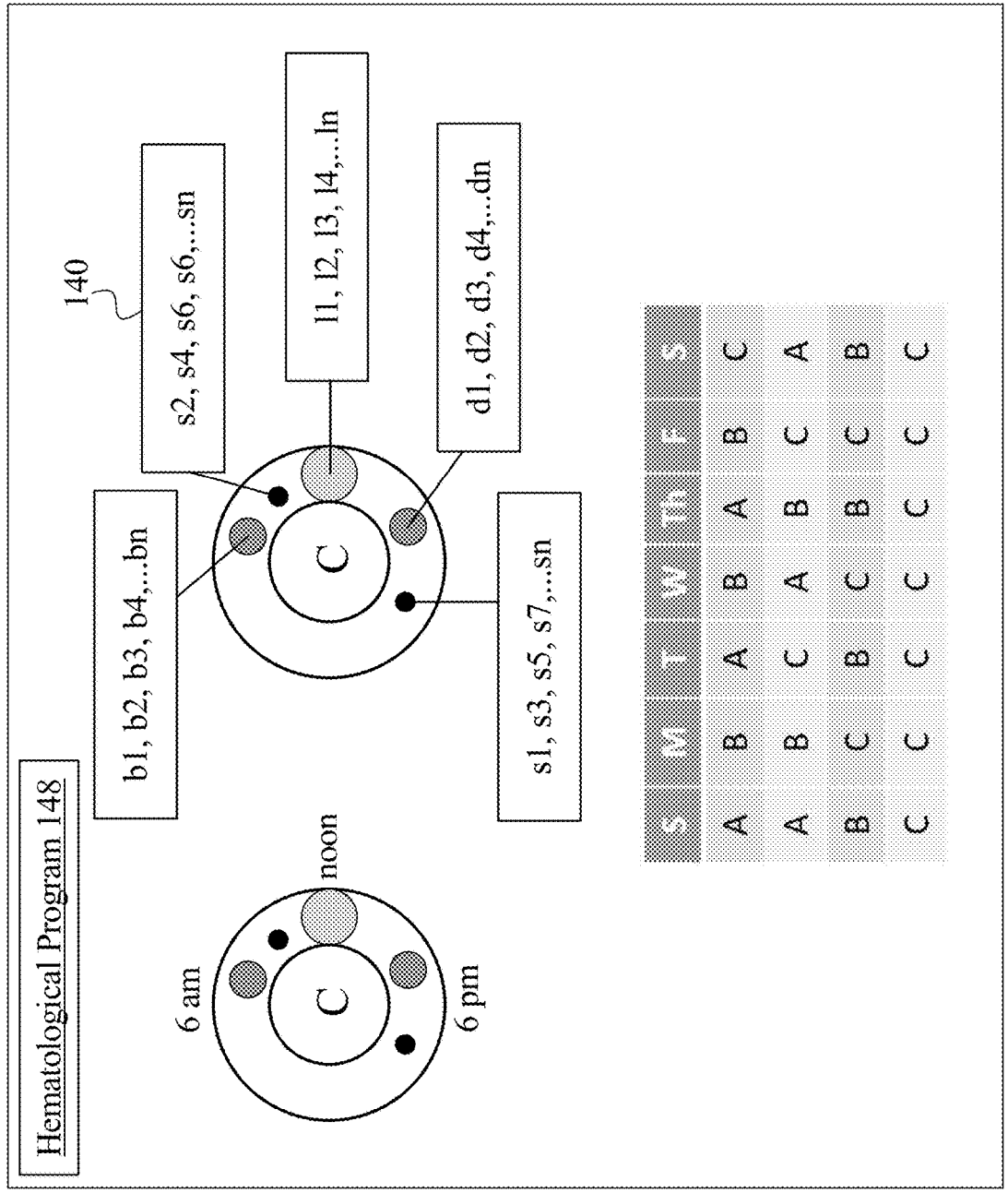
FIG. 5 is a diagrammatic representation of a hematological program.

Referring now to FIG. 5, a non-limiting exemplary embodiment 500 of a hematological program 148 is illustrated. Hematological program 148 may include a schedule for arranging nutrition elements 140, according to for instance a 24-hour timetable, as designated on the left, where consumption is planned along a subject's typical day-night cycle, beginning at ~ham until just after 6 pm. Nutrition element 140 may include breakfast (denoted as mid-sized dark grey circle), which may correspond to a file of breakfast-related plurality of nutrition elements 140 (denoted b1, b2, b3, b4 . . . bn, to the nth breakfast item). Nutrition element 140 may include snacks eaten throughout the day to, for instance achieve nutrient amounts missing from meals (denoted as small black circles), which may correspond to a file of snacking-related plurality of nutrition elements 140 (denoted s1, s2, s3, s4 . . . sn, to the nth snacking item). Nutrition element 140 may include dinner (denoted as large-sized light grey circle), which may correspond to a file of dinner-related plurality of nutrition elements 140 (denoted d1, d2, d3, d4 . . . dn, to the nth dinner item). Hematological program 148 may include a variety of custom diets, as denoted in the monthly schedule at the bottom, Sunday through Saturday. Hematological program 148 'C' is shown, which may be an idealistic goal for subject to achieve by the end of the month, where nourishment plan 'A' and 'B' are intermediate plans intended to wean subject to the 'ideal' plan. Nutrition elements 140 classified by category and may be further modified by 'A', 'B', 'C', and the like, according to subject preferences input into computing device 104. Circle sizes, denoting nutrition element 140 classes may relate to magnitude, which are graphed along the circle corresponding to the frequency they are expected to be consumed. Subject may indicate which nutrition element 140 from each category was consumed, and when it was consumed, to arrive at hematological score 152.

Figure 6:
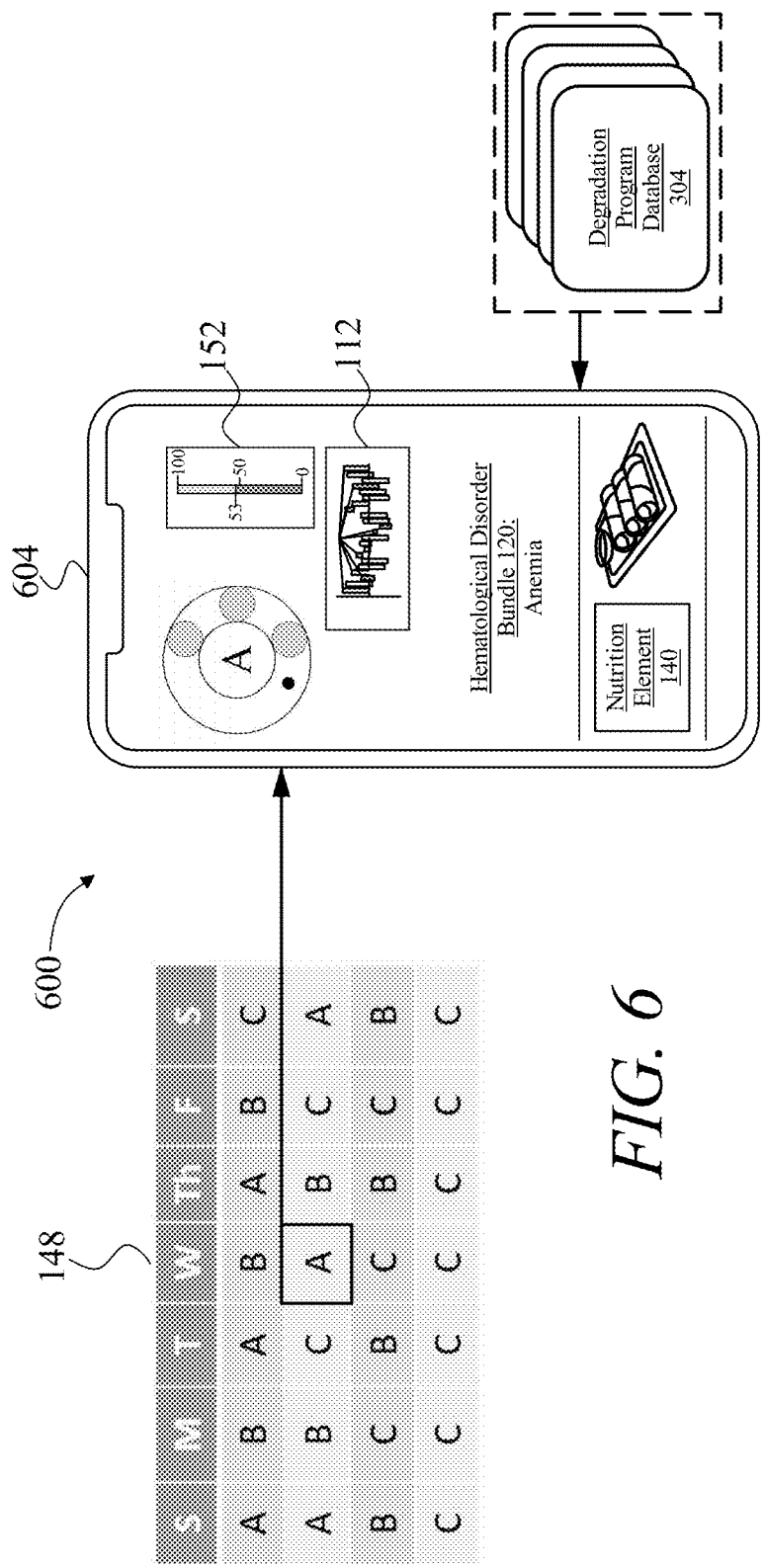
FIG. 6 is a diagrammatic representation of a subject device.

Referring now to FIG. 6, a non-limiting exemplary embodiment 600 of a subject device 604 is illustrated. Subject device 604 may include computing device 104, a "smartphone," cellular mobile phone, desktop computer, laptop, tablet computer, internet-of-things (IOT) device, wearable device, among other devices. Subject device 604 may include any device that is capable of communicating with computing device 104, hematological program database 304, or able to receive, transmit, and/or display, via a graphical user interface, hematological profile 112, nutrition element 140, hematological program 148, hematological score 152, among other outputs from system 100. Subject device 604 may provide a hematological profile 112, for instance as a collection of metrics determined from hematological datum 108 data. Subject device 604 may provide hematological disorder bundle 120 that was determined as a function of hematological classifier 124 and hematological profile 112. Subject device 604 may provide data concerning nutrient amounts, including the levels of specific nutrients, nutrient ranges, nutrients to avoid (for instance, if it exacerbates symptoms), and the like. Subject device 604 may link timing of foods to preemptive ordering interface for ordering a nutrition element 140, for instance and without limitation, through a designated mobile application, mapping tool or application, and the like, and a radial search method about a subject's current location as described in U.S. Nonprovisional application Ser. No. 17/087,745, filed Nov. 3, 2020, titled "A METHOD FOR AND SYSTEM FOR PREDICTING ALIMENTARY ELEMENT ORDERING BASED ON BIOLOGICAL EXTRACTION," the entirety of which is incorporated herein by reference. Subject device 604 may display nutrient elements 120 as a function of location, for instance and without limitation, as described in Subject device 604 may link nourishment consumption program 120 to a scheduling application, such as a 'calendar' feature on subject device, which may set audio-visual notifications, timers, alarms, and the like.

Figure 7:
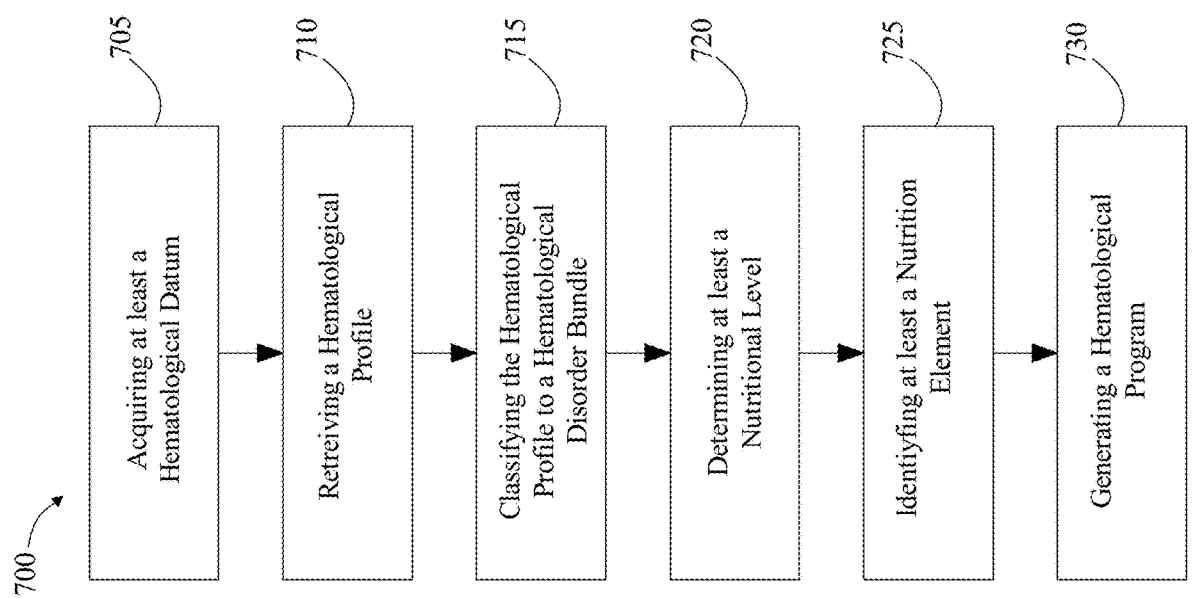
FIG. 7 is a block diagram of a method for generating a hematological program.

Referring now to FIG. 7, an exemplary embodiment 700 of a method for generating a hematological program for addressing hematological disorders using machine-learning is illustrated. At step 705, the method including acquiring, by a computing device 104, at least a hematological datum 108 relating to a subject; this may be implemented, without limitation, as described above in FIGS. 1-6.

Still referring to FIG. 7, at step 710, method includes retrieving, by the computing device 104, a hematological profile 112 related to the subject. Retrieving the hematological profile 112 related to the subject may include training a hematological machine-learning model 116 with training data that includes a plurality of data entries correlating hematological data to a plurality of hematological parameters and generating the hematological profile 112 as a function of the hematological profile machine-learning model 116 and at least the hematological datum 108; this may be implemented, without limitation, as described above in FIGS. 1-6.

Continuing in reference to FIG. 7, at step 715, method includes classifying, by the computing device 104, the hematological profile 112 to a hematological disorder bundle 120. Classifying the hematological profile 112 to a hematological disorder bundle 120 may include training a hematological classifier 124 using training data which includes a plurality of data entries of hematological profile data from a subset of categorized subjects, classifying the hematological profile 112 to the hematological disorder bundle 120 using the hematological classifier 124. Classifying may include classifying the hematological profile 112 to a nutrition-linked hematological disorder bundle. Classifying may include classifying the hematological profile 112 to a nutrition-linked disorder prevention bundle; this may be implemented, without limitation, as described above in FIGS. 1-6.

Continuing in reference to FIG. 7, at step 720, method includes determining, by the computing device 104, using the hematological disorder bundle 120 and the hematological profile 112, at least a nutritional level 128, wherein determining the at least a nutritional level 128 includes identifying a hematological relationship 132, wherein the hematological relationship 132 relates an effect of a plurality of nutritional levels 128 on the data in the hematological profile 112 that relates to the hematological disorder bundle 120 and determining the at least a nutritional level as a function of the hematological relationship and the hematological profile. Determining the hematological relationship 132 may include generating a hematologic model 132 by using training data, wherein training data includes a plurality of data entries correlating nutritional levels to effects on hematological data and determining the hematological relationship as a function of the hematologic model and the hematological profile; this may be implemented, without limitation, as described above in FIGS. 1-6.

Continuing in reference to FIG. 7, at step 725, method includes identifying, by the computing device 104, using the at least a nutritional level 128, at least a nutrition element 140. Identifying the at least a nutrition element 140 may include generating a nutrition model 144 using training data including a plurality of data entries of nutrition levels 128 correlating to nutrition elements 140 and determining the at least a nutrition element as a function of the nutrition model and the at least a nutritional level. Identifying at least a nutrition element 140 may include retrieving a plurality of nutrition elements from a data repository as a function of the at least a nutritional level 128; this may be implemented, without limitation, as described above in FIGS. 1-6.

Continuing in reference to FIG. 7, at step 730, method includes generating, by the computing device 104, a hematological program 148 using the at least a nutrition element 140, wherein the hematological program 148 includes a consumption program. Generating the hematological program 148 may include generating a linear programming function with the plurality of nutrition elements wherein the linear programming function outputs at least an ordering of the plurality of nutrition elements according to the nutritional level 128. The hematological program 148 may include a hematological score; this may be implemented, without limitation, as described above in FIGS. 1-6.

It is to be noted that any one or more of the aspects and embodiments described herein may be conveniently implemented using one or more machines (e.g., one or more computing devices that are utilized as a subject computing device for an electronic document, one or more server devices, such as a document server, and the like) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methods and/or embodiments described herein. Examples of a machine-readable storage medium include, but are not limited to, a magnetic disk, an optical disc (e.g., CD, CD-R, DVD, DVD-R, and the like), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, and the like), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
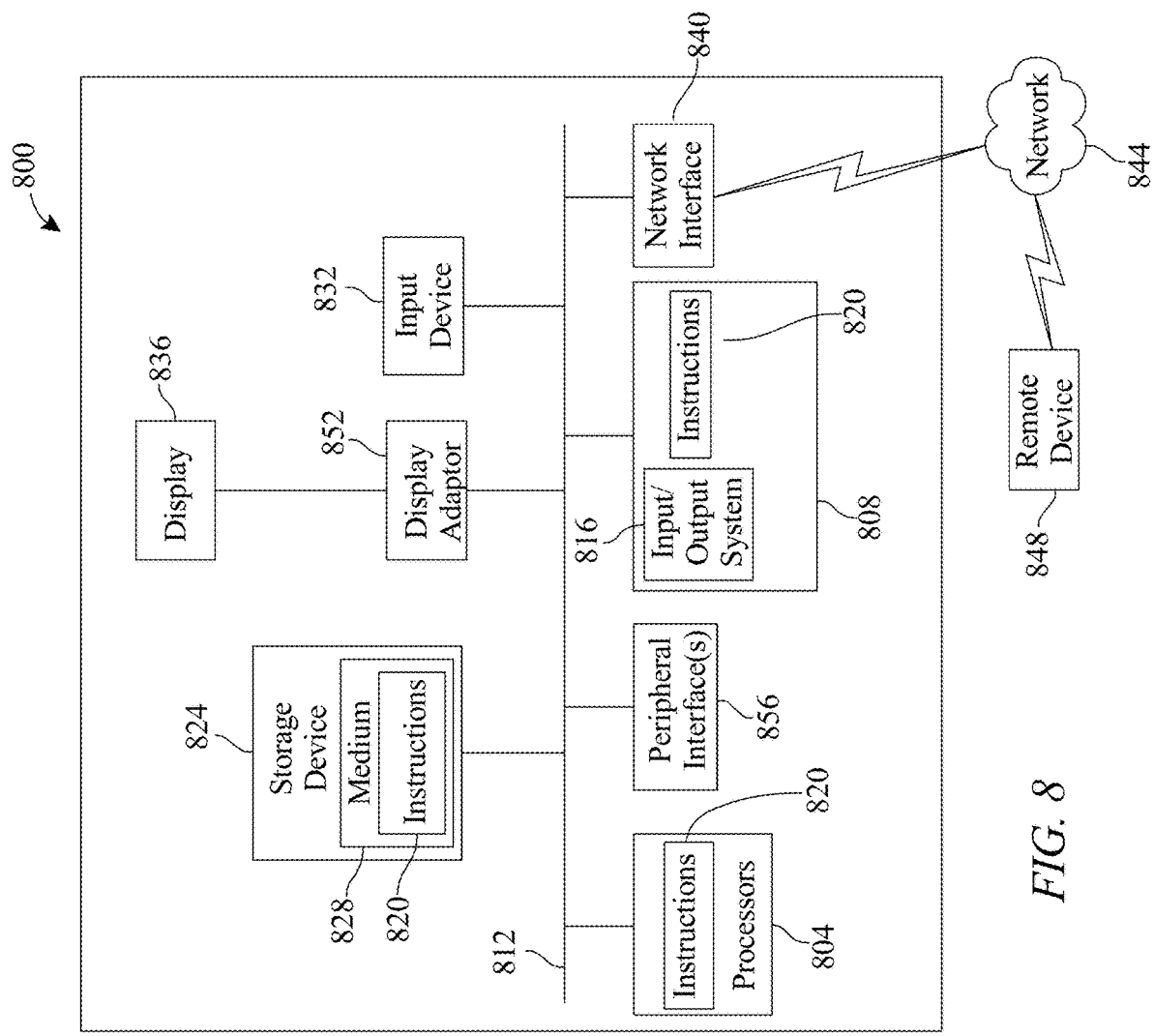
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a micro-controller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a subject of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, and the like), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a subject selection device for selecting one or more graphical representations in a graphical interface as described above.

A subject may also input commands and/or other information to computer system 800 via storage device 824 (e.g., a removable disk drive, a flash drive, and the like) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, and the like) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for generating a program for addressing hematological disorders using machine-learning, the system comprising:
   a computing device, wherein the computing device is configured to:
   acquire at least a hematological datum relating to a subject;
   receiving training data as a function of a machine-learning process, wherein the training data comprises hematological data correlating to a plurality of hematological parameters, wherein the training data is iteratively updated using outputs of the plurality of hematological parameters of previous iterations as inputs to subsequent iterations, wherein the plurality of hematological parameters comprises at least a numerical value for biomarkers relating to a health of the subject and a nutrient amount;
   generating a hematological machine-learning model as a function of the iteratively updated training data, wherein the hematological machine learning model comprises an input layer of nodes, at least one intermediate layers, and an output layer of nodes, wherein the connections between nodes in adjacent layers are adjusted to output values at the output nodes;
   train the hematological machine-learning model iteratively as a function of the training data;
   generate a hematological profile related to the subject as a function of the trained hematological machine-learning model and the at least a hematological datum;
   deriving, using the trained hematological machine learning model, a numerical scale for providing the numerical value to the hematological profile and a hematological score, wherein the hematological machine learning model learns an upper and lower limits to the numerical scale, an increment to providing scoring, and a criteria for increasing and decreasing the upper and lower limits encompassed in the hematological profile and the hematological score;
   updating automatically the hematological score as a function of the trained hematological machine learning model and the iteratively updated training data using outputs of the plurality of hematological parameters;
   classify the hematological profile to a hematological disorder bundle, wherein classifying the hematological profile comprises training a hematological classification machine-learning process as a function of a plurality of data values relating the numerical value for biomarkers and the nutrient amount relating to the health of the subject to the hematological disorder bundle; generating a hematological classifier as a function of the hematological classification machine-learning process; and classifying the hematological profile to the hematological disorder bundle as a function of the hematological classifier;
   determine, using the hematological disorder bundle and the hematological profile, at least a nutritional level, wherein determining the at least a nutritional level includes:
      identifying a hematological relationship, wherein the hematological relationship relates an effect of a plurality of nutritional levels on the hematological disorder bundle; and
      determining the at least a nutritional level as a function of the hematological relationship;
   identify, using the at least a nutritional level, at least a nutrition element;
   generate a hematological program as a function of the at least a nutrition element, wherein the hematological program selects the at least a nutritional element as a function of a threshold score and a subject preference, wherein the hematological program selects the at least a nutritional element above the threshold score; and generate a consumption program based on the at least a nutrition element and the hematological program.

2. The system of claim 1, wherein retrieving the hematological profile further comprises:

generating the hematological profile as a function of the hematological profile machine-learning model and the at least a hematological datum.

3. The system of claim 1, wherein classifying the hematological profile to the hematological disorder bundle further comprises:

training a hematological classifier using training data which includes a plurality of data entries of hematological profile data from a subset of categorized subjects.

4. The system of claim 3, wherein classifying includes classifying the hematological profile to a nutrition-linked hematological disorder bundle.

5. The system of claim 3, wherein classifying includes classifying the hematological profile to a nutrition-linked disorder prevention bundle.

6. The system of claim 1, wherein determining the hematological relationship further comprises:

generating a hematologic model using training data, wherein training data includes a plurality of data entries correlating nutritional levels to effects on hematological data; and determining the hematological relationship as a function of the hematologic model and the hematological profile.

7. The system of claim 1, wherein identifying the at least a nutrition element further comprises:

generating a nutrition model using training data including a plurality of data entries of nutrition levels correlating to nutrition elements; and determining the at least a nutrition element as a function of the nutrition model and the at least a nutritional level.

8. The system of claim 1, wherein identifying at least a nutrition element further comprises retrieving a plurality of nutrition elements from a data repository as a function of the at least a nutritional level.

9. The system of claim 8, wherein generating the program for addressing hematological disorders further comprises generating a linear programming function with the plurality of nutrition elements wherein the linear programming function outputs at least an ordering of the plurality of nutrition elements according to the nutritional level.

10. The system of claim 1, wherein the program for addressing hematological disorders includes a hematological score.

11. A method for generating a program for addressing hematological disorders using machine-learning, the method comprising:

acquiring, by a computing device, at least a hematological datum relating to a subject;

receiving training data as a function of a machine-learning process, wherein the training data comprises hematological data correlating to a plurality of hematological parameters, wherein the training data is iteratively updated using outputs of the plurality of hematological parameters of previous iterations as inputs to subsequent iterations, wherein the plurality of hematological parameters comprises at least a numerical value for biomarkers relating to a health of the subject and a nutrient amount;

generating a hematological machine learning model as a function of the iteratively updated training data, wherein the hematological machine learning model comprises an input layer of nodes, at least one intermediate layers, and an output layer of nodes, wherein the connections between nodes in adjacent layers are adjusted to output values at the output nodes;

training the hematological machine-learning model iteratively as a function of the training data;

generating a hematological profile related to the subject as a function of the trained hematological machine-learning model and the at least a hematological datum;

deriving, using the trained hematological machine learning model, a numerical scale for providing numerical values to the hematological profile and a hematological score, wherein the hematological machine learning model learns the upper and lower limits to the numerical scale, an increment to providing scoring, and a criteria for increasing and decreasing the upper and lower limits encompassed in the hematological profile and the hematological score;

updating automatically the hematological score as a function of the trained hematological machine learning model and the iteratively updated training data using outputs of the plurality of hematological parameters;

classifying, by the computing device, the hematological profile to a hematological disorder bundle, wherein classifying the hematological profile comprises training a hematological classification machine-learning process as a function of a plurality of data values relating the numerical value for biomarkers and the nutrient amount relating to the health of the subject to the hematological disorder bundle; generating a hematological classifier as a function of the hematological classification machine-learning process; and classifying the hematological profile to the hematological disorder bundle as a function of the hematological classifier;

determining, by the computing device, using the hematological disorder bundle and the hematological profile, at least a nutritional level, wherein determining the at least a nutritional level includes:

identifying a hematological relationship, wherein the hematological relationship relates an effect of a plurality of nutritional levels on the hematological disorder bundle; and determining the at least a nutritional level as a function of the hematological relationship and the hematological profile;

identifying, by the computing device, using the at least a nutritional level, at least a nutrition element;

generating, by the computing device, a hematological program as a function of the at least a nutrition element, wherein the hematological program selects the at least a nutritional element as a function of a threshold score and a subject preference, wherein the hematological program selects the at least a nutritional element above the threshold score; and generating, by the computing device, a consumption program as a function of the at least a nutrition element and the hematological program.

12. The method of claim 11, wherein retrieving the hematological profile related to the subject further comprises:

generating the hematological profile as a function of the hematological profile machine-learning model and at least the hematological datum.

13. The method of claim 11, wherein classifying the hematological profile to a hematological disorder bundle further comprises:
    training a hematological classifier using training data which includes a plurality of data entries of hematological profile data from a subset of categorized subjects.

14. The method of claim 13, wherein classifying includes classifying the hematological profile to a nutrition-linked hematological disorder bundle.

15. The method of claim 13, wherein classifying includes classifying the hematological profile to a nutrition-linked disorder prevention bundle.

16. The method of claim 11, wherein determining the hematological relationship further comprises:
    generating a hematologic model by using training data, wherein training data includes a plurality of data entries correlating nutritional levels to effects on hematological data; and
    determining the hematological relationship as a function of the hematologic model and the hematological profile.

17. The method of claim 11, wherein identifying the at least a nutrition element further comprises:
    generating a nutrition model using training data including a plurality of data entries of nutrition levels correlating to nutrition elements; and
    determining the at least a nutrition element as a function of the nutrition model and the at least a nutritional level.

18. The method of claim 11, wherein identifying at least a nutrition element further comprises retrieving a plurality of nutrition elements from a data repository as a function of the at least a nutritional level.

19. The method of claim 18, wherein generating the program for addressing hematological disorders further comprises generating a linear programming function with the plurality of nutrition elements wherein the linear programming function outputs at least an ordering of the plurality of nutrition elements according to the nutritional level.

20. The method of claim 11, wherein the program for addressing hematological disorders includes a hematological score.

* * * * *